(12) United States Patent
Goetz

(10) Patent No.: US 9,348,974 B2
(45) Date of Patent: May 24, 2016

(54) REMOTE MANAGEMENT OF THERAPY PROGRAMMING

(75) Inventor: Steven M. Goetz, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 1274 days.

(21) Appl. No.: 12/682,923

(22) PCT Filed: Sep. 29, 2008

(86) PCT No.: PCT/US2008/078134
§ 371 (c)(1),
(2), (4) Date: Apr. 14, 2010

(87) PCT Pub. No.: WO2009/055207
PCT Pub. Date: Apr. 30, 2009

(65) Prior Publication Data
US 2010/0222845 A1 Sep. 2, 2010

Related U.S. Application Data

(60) Provisional application No. 61/000,144, filed on Oct. 24, 2007.

(51) Int. Cl.
*A61N 1/00* (2006.01)
*G06F 19/00* (2011.01)
(Continued)

(52) U.S. Cl.
CPC ........ *G06F 19/3456* (2013.01); *A61N 1/37252* (2013.01); *G06F 19/3406* (2013.01);
(Continued)

(58) Field of Classification Search
USPC .......................................................... 607/59
See application file for complete search history.

(56) References Cited

U.S. PATENT DOCUMENTS

| 6,044,297 | A | 3/2000 | Sheldon et al. | |
| 6,381,496 | B1 * | 4/2002 | Meadows et al. | 607/59 |

(Continued)

FOREIGN PATENT DOCUMENTS

| EP | 1491234 | 12/2004 |
| WO | WO96/22125 | 7/1996 |

(Continued)

OTHER PUBLICATIONS

PCT/US08/78134: Search Report and Written Opinion dated Jun. 9, 2009.

(Continued)

*Primary Examiner* — Amanda Patton
*Assistant Examiner* — Philip C Edwards
(74) *Attorney, Agent, or Firm* — Shumaker & Sieffert, P.A.

(57) ABSTRACT

The disclosure is directed to techniques for remote management of information relating to therapy delivered to a patient by an implantable medical device (IMD). A remote monitoring system for therapy programming includes an IMD that delivers therapy, e.g., neurostimulation, drug therapy, or both, to a patient, an external programming device associated with the IMD, such as a patient programmer, and a remote networking device that receives usage information from the external programming device. The external programming device communicates with the IMD via local, wireless communication, and the remote networking device receives usage information from the external programming device via a network. The usage information includes information that relates to use of therapy by the patient, use of features of the external programming device and the IMD, or use of navigation patterns of a user interface of the external programming device.

23 Claims, 13 Drawing Sheets

(51) Int. Cl.
*G06Q 50/24* (2012.01)
*A61N 1/372* (2006.01)

(52) U.S. Cl.
CPC ............ *G06F19/3481* (2013.01); *G06Q 50/24* (2013.01); *A61B 2560/0271* (2013.01); *A61N 1/37247* (2013.01); *A61N 1/37264* (2013.01); *A61N 1/37282* (2013.01); *G06F 19/3418* (2013.01)

(56) References Cited

U.S. PATENT DOCUMENTS

| | | | |
|---|---|---|---|
| 6,662,052 | B1 | 12/2003 | Sarwal et al. |
| 2001/0031997 | A1 | 10/2001 | Lee |
| 2002/0029002 | A1 | 3/2002 | Bardy |
| 2002/0143372 | A1 | 10/2002 | Snell et al. |
| 2002/0183693 | A1 | 12/2002 | Peterson et al. |
| 2006/0020292 | A1* | 1/2006 | Goetz et al. ............... 607/2 |
| 2006/0089592 | A1 | 4/2006 | Kadhiresan et al. |
| 2006/0235289 | A1 | 10/2006 | Wesselink |
| 2007/0142868 | A1 | 6/2007 | Moon et al. |

FOREIGN PATENT DOCUMENTS

| | | |
|---|---|---|
| WO | WO2004/067083 | 8/2004 |
| WO | WO2004/093989 | 11/2004 |
| WO | WO2006/099035 | 9/2006 |
| WO | WO2007/079543 | 7/2007 |
| WO | WO2007/112092 | 10/2007 |
| WO | WO2009/055202 | 4/2009 |
| WO | WO2009/055204 | 4/2009 |
| WO | WO2009/055205 | 4/2009 |
| WO | WO2009/055206 | 4/2009 |
| WO | WO2009/055207 | 4/2009 |

OTHER PUBLICATIONS

PCT/US08/78134: Response to Written Opinion filed Sep. 9, 2009.
PCT/US08/78134: 2$^{nd}$ Written Opinion dated Feb. 5, 2010.
PCT/US08/78134: Response to 2$^{nd}$ Written Opinion dated Apr. 5, 2010.
PCT/US08/78134: IPRP dated Apr. 22, 2010.
PCT/US08/78099: Search Report and Written Orinion dated Dec. 11, 2008.
PCT/US08/78099: Response to Written Opinion dated Aug. 14, 2009.
PCT/US08/78099: IPRP dated Feb. 2, 2010.
PCT/US08/78125: Search Report and Written Opinion dated Feb. 2, 2009.
PCT/US08/78114: Search Report and Written Opinion dated Feb. 10, 2009.
PCT/US08/78114: Response to Written qpinion dated Aug. 21, 2009.
PCT/US08/78114: IPRP dated Dec. 18, 2009.
PCT/US08/78127: Search Report ard Written Opinion dated Dec. 12, 2008.
PCT/US08/78127: Response to Written Opinion dated Jun. 12, 2009.
PCT/US08/78127: IPRP dated Dec. 21, 2009.

* cited by examiner

REMOTE MANAGEMENT OF THERAPY PROGRAMMING

This application is a U.S. National Stage filing under 35 U.S.C. 371 of PCT Application Serial No. PCT/US2008/078134, filed Sep. 29, 2008, which claims priority to U.S. Provisional Application No. 61/000,144 filed Oct. 24, 2007, entitled "Remote Management of Therapy Programming" the disclosures of each of the above which are incorporated by reference as if re-written herein in their entirety.

TECHNICAL FIELD

The invention relates to the delivery of therapy by medical devices and, more particularly, to programming the delivery of therapy by medical devices.

BACKGROUND

Medical devices that deliver a therapy to a patient often do so according to a program that includes a plurality of parameters. Each of the parameters of such a program defines an aspect of the therapy as delivered by the medical device according to that program. For example, the programs used by medical devices that deliver therapy in the form of electrical stimulation, such as neurostimulators, typically include parameters that define characteristics of the electrical stimulation waveform to be delivered. Where electrical stimulation is delivered in the form of electrical pulses, for example, the parameters for such a program may include a voltage or current amplitude, a pulse width, and a rate at which the pulses are to be delivered by the medical device. Further, where a medical device that delivers electrical stimulation is implantable and, as is typical for implantable neurostimulators, coupled to an electrode set including a plurality of electrodes, such a program may include an indication of the particular electrodes within the electrode set to be used to deliver the pulses, and the polarities of the selected electrodes. As another example, the programs used by medical devices that deliver therapy via infusion of a drug or other agent may include parameters that define flow rates, agent types or concentrations, and infusion type, e.g., continuous or bolus. When a medical device that delivers therapy via infusion of a drug or other agent utilizes bolus infusion, additional program parameters may include the number of boluses per day and the times of the bolus delivery.

In most cases, a clinician creates the one or more programs that a medical device will use to deliver therapy to a patient during an initial programming session. In the case of implantable medical devices, the initial programming session typically occurs shortly after the device is implanted in the patient. The values for each of the parameters of a program may have a significant impact on the efficacy and side effects of the delivery of therapy according to that program. The process of selecting values for the parameters that provide adequate results can be time consuming. In particular, the process may require a great deal of trial and error testing of numerous potential combinations of parameter values before a "best" program is discovered. A "best" program may be a program that is better in terms of clinical efficacy versus side effects experienced than other programs tested. The process is particularly burdensome in the case of programming implantable neurostimulators for delivery of spinal cord stimulation (SCS) therapy, which are often coupled to an electrode set including eight or sixteen electrodes. The number of possible combinations of electrodes that could be tested during a programming session from set of that size is substantial, e.g., potentially on the order of tens or hundreds of thousands, or even millions of possible electrode combinations.

In some cases, the clinician may test combinations of parameter values, i.e., potential programs, by manually specifying each combination to test based on intuition or some idiosyncratic methodology, and recording notes on the efficacy and side effects of each combination after delivery of stimulation according to that combination. During a programming session, the clinician may be required to make notations describing the parameters of a number of tested programs and feedback received from the patient regarding the perceived efficacy side effects of each program. The clinician may then select the "best" program based on the notations.

Even after this often-lengthy process, the programs selected during an initial programming session may ultimately prove to be inadequate. The eventual inadequacy of the initial programming may be due to a variety of problems, including progression of symptoms and/or an underlying ailment, increased or changed symptoms or side effects during activities and/or postures that were not replicated in the clinic during the initial programming session, slow onset of side effects and, in the case of delivery of stimulation via electrodes located on implantable leads, lead migration. If the programs selected during an initial programming session prove to be inadequate, the patient must return to the clinic for a follow-up programming session. Multiple follow-up programming sessions may be required over the period of time that the medical device is used to deliver therapy to the patient.

During a follow-up programming session, the clinician may refer to any printed records, or his or her own memory of the previous programming sessions, i.e., of the previously tested programs and their efficacy and side effects. However, printed records and clinician memory of previous programming sessions are often absent or inadequate, and provide little assistance in more quickly identifying desirable programs during a current programming session. Consequently, the clinician typically must start the time-consuming program selection process anew during each follow-up programming session.

SUMMARY

In general, the invention is directed to techniques for remote management of information relating to therapy delivered to a patient by an implantable medical device (IMD). A remote monitoring system for therapy programming includes an IMD that delivers therapy, e.g., neurostimulation, drug therapy, or both, to a patient, an external programming device associated with the IMD, such as a patient programmer, and a remote networking device that receives usage information from the external programming device. The external programming device communicates with the IMD via local, wireless communication and the remote networking device receives usage information from the external programming device via a network, e.g., a wide area network (WAN) such as the Internet.

The IMD delivers therapy to the patient according to one or more programs. A group of programs may be referred to as a "parameter set" or "program group." Each program of a group may include different values for a plurality of parameters, such as amplitude, pulse width, pulse rate, and electrode configuration. In an embodiment in which the IMD delivers therapy via infusion of a drug or other agent, parameters may include flow rates, agent types or concentrations, and infusion type, e.g., continuous or bolus. The IMD may deliver therapy according to a program group by cycling through the constituent programs, e.g., delivering one or more stimulation pulses or agents according to a first program of the program group, then the second program of the group, and so on. A number of program groups may be assembled into one or more lists of program groups and stored in the IMD, the patient programmer, or both. The patient may use the patient programmer to select a list of program groups, and then a program group within the list. The IMD may use the selected program group to deliver therapy to the patient.

The patient may also use the patient programmer to make adjustments to individual programs or program groups. The patient programmer may display the parameters for one or more programs, and the patient may adjust one or more parameter values within ranges established by a clinician. The patient may also have the option of making a global adjustment of a parameter value across each of the programs within a program group, e.g., by adjusting the pulse amplitude for each program within the program group. The adjusted program or programs may be stored for later use by the patient. In pump therapies, the patient may have the ability to administer a bolus of drug or other agent a prescribed number of times a day or may be able to adjust a continuous or basal flow rate within prescribed ranges.

One or both of the IMD and the patient programmer may record usage information relating to the use of therapy by the patient. The usage information may include information relating to the use of program groups or individual programs by the patient, adjustments to programs or groups by the patient, and the overall use of neurostimulation therapy. Patient programmer user interface navigation patterns and feature use may also be recorded.

The remote networking device may be a server that maintains a database and receives the usage information from the external programming device via a network that includes one or more of a local area network (LAN), a wide area network (WAN), a landline telephone network, a cellular telephone network, the Internet, and a wireless network. The remote networking device may receive the usage information on a periodic basis, such as according to a schedule, on demand, on an opportunistic basis, or in real-time. Where the remote networking device receives usage information on a periodic basis, the patient programmer may initiate the transfer of usage information. Where the remote networking device receives the usage information on an on demand basis, that patient or clinician may initiate the transmission of usage information from the patient programmer to the remote networking device. Where the remote networking device receives the usage information in real-time, the patient and clinician may interact with each other over the network.

In some example embodiments, the patient programmer may connect directly to the network to transmit locally stored usage information and usage information collected from the IMD to the remote networking device. In other example embodiments, the patient programmer may connect to a desktop or laptop computer, a personal digital assistant (PDA), a cellular phone, or the like that is connected to the network and use the network connection of the computing device to transmit usage information to the remote networking device. In additional example embodiments, the patient programmer may connect to the network via a docking station that recharges the programmer and serves other functions.

The remote networking device may display the usage information to a user, such as a clinician, a technician, or a manufacturer. The user may view the usage information on a display of a computing device, such as a desktop or laptop computer, workstation, PDA, or the like, connected to the remote networking device. For example, the remote networking device may display the usage information as a histogram that illustrates percentages of a period of time that each program or program group was used to provide therapy at various times throughout the day, a diagram that illustrates when various parameter adjustments occurred, the parameters adjusted, and the adjusted parameter values, and a diagram that illustrates the overall usage of therapy during consecutive time periods. For pump therapies, the remote networking device may display the number and timing of patient administered bolus infusions and any changes to the basal rate that occurred. A clinician may use these diagrams to select programs for use in long term programming of the IMD or modify program groups, programs, or therapy parameters. A clinician may also use these diagrams to identify unexpected or undesirable therapy patterns, such as patient initiated therapy patterns that indicate drug seeking behavior or therapy patterns that indicate lack of use of particular programs, or therapy in general.

In an additional example, a manufacturer may view usage information that relates to navigation patterns of the user interface of the patient programmer and use of features of the patient programmer. The remote networking device or associated computing device may display this usage information as a diagram, a chart, a graph, or other graphical representation of the information. In this case, it may be desirable to illustrate the number of times or frequency that one or more features have been used. The manufacturer may view this usage information in future product development efforts to provide more user friendly patient programmers to patients.

Instead of or in addition to presenting the usage information to a user for review, the remote networking device may also analyze the usage information and suggest actions based on the analysis. For example, the remote networking device may analyze usage information relating to the use of therapy by the patient and suggest therapy options or modifications to the therapy based on the analysis. In particular, the remote networking device may identify frequently used programs or program groups and suggest therapy options that are similar to programs or groups. In pump systems, the remote networking device might suggest automatic bolus administration to match the timing of patient administered bolus infusions that occurred at regular or periodic intervals. The remote networking device may also suggest additional programs by comparing frequently-used programs to programs tested on the patient during a programming session or a program library that stores a plurality of programs according to a set of hierarchical categories. Further, the remote networking device may also remove infrequently used programs or groups from a list of available programs or groups.

In one embodiment, the invention provides a system comprising a patient device that records usage information relating to the use, by a patient, of a therapy delivered by an implantable medical device to the patient, and a remote networking device that receives the usage information from the patient device via a network.

In another embodiment, the invention provides a method comprising recording, in a patient device, usage information relating to the use, by a patient, of a therapy delivered by an implantable medical device to the patient, and transmitting the usage information from the patient device to a remote networking device via a network.

The invention may provide a number of advantages. For example, by receiving usage information over a wide area network, the remote networking device may at least partially reduce the burden on the patient programmer and IMD to store usage information. This also allows a clinician or other authorized user to view the usage information for a plurality of patients in various locations around the world which may provide improved service for any particular patient.

In addition, the recollection of the patient as to which programs or program groups were preferred and the manner in which therapy was used is often inaccurate. However, storing usage information provides an objective and accurate record of use of therapy. The objectivity of stored usage information may make it more likely that changes to the therapy made by the clinician will result in more effective therapy for the patient. Stored usage information may also allow a clinician to more easily identify therapy misuse, such as unexpected or undesirable therapy patterns and misuse due to lack of training. Moreover, presenting stored usage information to a clinician or other authorized user with various summaries, diagrams, histograms, and the like may allow the users to more easily interpret the usage information.

Further, automatically analyzing the usage information and providing suggestions to the user based on the analysis may provide improved therapy to the patient and reduce the amount of time necessary for the clinician to provide effective follow-up programming of the IMD. Analyzing usage information may also increase patient satisfaction with the IMD system and the therapy.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
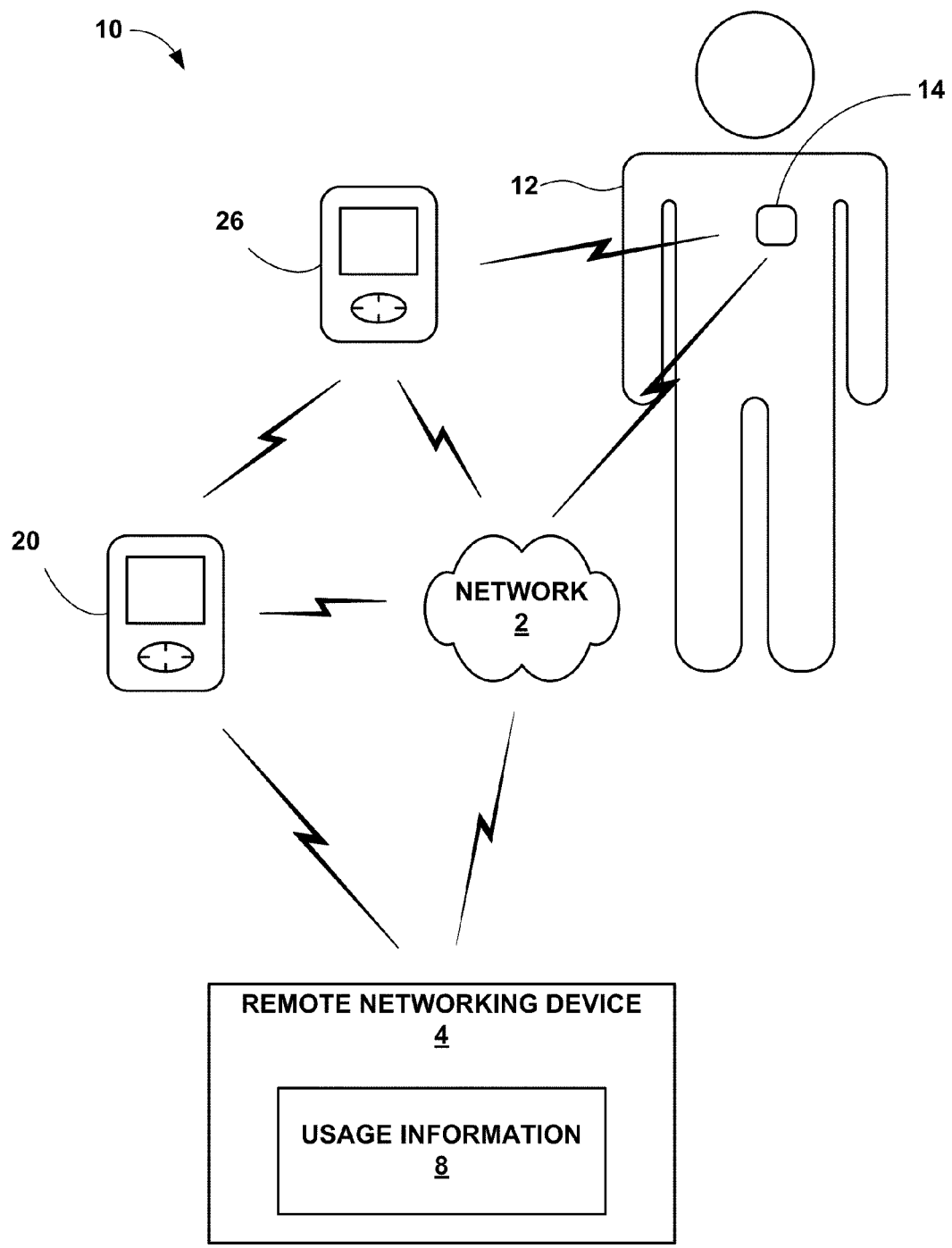
FIG. 1 is a conceptual diagram illustrating an example system that includes a remote networking device for managing usage information.

FIG. 1 is a diagram illustrating an example system 10 for managing delivery of therapy to a patient 12 and usage information 8. System 10 includes an implantable medical device (IMD) 14 that delivers therapy to patient 12, a clinician programmer 20, a patient programmer 26, and a remote networking device 4 that receives usage information 8 from IMD 14, patient programmer 26, or both via a network 2. IMD 14 may deliver neurostimulation therapy, drug therapy, or both to patient 12. Accordingly, IMD 14 may be an implantable pulse generator that delivers neurostimulation therapy to patient 12 in the form of electrical pulses, an implantable drug pump that delivers a drug or other agent to patient 12 via a catheter, e.g., for alleviation of pain by intrathecal drug delivery, or a device or devices that delivers both neurostimulation therapy and drug therapy to patient 12.

IMD 14 delivers therapy according to one or more programs. Each program may include values for a number of parameters, and the parameter values define the therapy delivered according to that program. In embodiments where IMD 14 delivers neurostimulation therapy in the form of electrical pulses, the parameters may include voltage or current pulse amplitudes, pulse widths, pulse rates, electrode combinations, polarities of selected electrodes, and the like. In embodiments where IMD 14 includes a drug pump instead of or in addition to a neurostimulator, program parameters may define flow rates, agent types or concentrations, or infusion types, e.g., continuous or bolus. In embodiments in which IMD 14 includes a drug pump that utilizes bolus infusion, additional program parameters may include the number of boluses per day and the times of the bolus delivery.

Generally, patient programmer 26 or IMD 14 stores programs selected during a programming session. A clinician may select programs during a programming session using clinician programmer 20 by specifying one or more programs, e.g., by selecting parameter values for one or more programs, to be used by IMD 14 for delivery of therapy to patient 12. During a programming session a number of programs are tested on patient 12, e.g., clinician programmer 20 directs IMD 14 to deliver therapy to patient 12 according to each program. The clinician selects one or more of the tested programs for use by IMD 14 in delivering therapy to patient 12 and transmits the selected programs to patient programmer 26 or IMD 14. Where the programs are stored in patient programmer 26, patient programmer 26 may transmit programs selected by patient 12 to IMD 14 for delivery of therapy to patient 12 according to the selected program. Where the programs are stored in IMD 14, patient programmer 26 may display a list of programs stored within IMD 14 to patient 12, and transmit an indication of the selected program to IMD 14 for delivery of therapy to patient 12 according to the selected program.

Patient 12 may use patient programmer 26 to control the delivery of therapy by IMD 14. In particular, patient 12 may use patient programmer 26 to activate or deactivate therapy and, as will be described below, use patient programmer 26 to select which from among a plurality of available programs will be used by IMD 14 to deliver therapy or to self administer prescribed therapy regimes. Further, as will be described below, patient programmer 26 may send usage information 8 to remote networking device 4 via network 2 during times between clinic visits.

IMD 14, clinician programmer 20, and patient programmer 26 may, as shown in FIG. 1, communicate with each other via local wireless communication. During a programming session in which clinician programmer 20 is used to program therapy, clinician programmer 20 and patient programmer 26 may, for example, communicate via wireless communication with IMD 14 using RF telemetry techniques known in the art. Clinician programmer 20 and patient programmer 26 may communicate with each other using any of a variety of local wireless communication techniques, such as radio-frequency (RF) communication according to the 802.11 or Bluetooth specification sets, infrared communication according to the IRDA specification set, or other standard or proprietary telemetry protocols. Clinician programmer 20 and patient programmer 26 need not communicate wirelessly, however. For example, clinician programmer 20 and patient programmer 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, communicating via a local area network (LAN), wide area network (WAN), public switched telephone network (PSTN), or cellular telephone network, for example.

As will be described in detail below, patient programmer 26, IMD 14, or both record usage information 8 during normal operation, i.e., during operation outside of a clinical environment. Remote networking device 4 receives usage information 8 from patient programmer 26 and/or IMD 14 via network 2 and may present usage information 8 to a user. Remote networking device 4 may also, in some example embodiments, analyze usage information 8 and take action or suggest action to the user based on the analysis. As one example, remote networking device 4 may analyze usage information 8 to identify abrupt changes from an established pattern of usage, e.g., usage reflective of typical or prescribed therapy for a particular patient. The term "usage information" in this disclosure refers to use of system 10 by patient 12. Usage information may include information that relates the use of therapy by patient 12, such as the use of individual programs or groups of programs by patient 12, adjustments to programs or groups, and overall use of therapy by patient 12. Usage information may also include information that relates to navigation patterns of a user interface of patient programmer 26 and feature use of patient programmer 26, as well as information relating to the performance of IMD 14 and patient programmer 26.

In FIG. 1, patient programmer 26 and IMD 14 communicate with remote networking device 4 via network 2 which may include one or more of a local area network (LAN), a wide area network (WAN), a landline telephone network, a cellular phone network, the Internet, and a wireless network. In particular, remote networking device 4 receives usage information from at least one of IMD 14 and patient programmer 26 over network 2. Where remote networking device 4 receives usage information 8 from IMD 14, IMD 14 may connect directly to network 2 or may connect to network 2 via a link device, such as a wireless modem, a base station that provides, for example, recharge features and other features for patient programmer 26, a laptop or desktop computer, or other computing device with a connection to network 2. Where remote networking device 4 receives usage information 8 from patient programmer 26, patient programmer 26 may directly connect to network 2 via a wired or wireless connection or may connect to network 2 via a link device as described with respect to IMD 14. Furthermore, in some embodiments, IMD 14 sends information to network 2 through patient programmer 26, i.e., through a telemetric communication with the patient programmer, which in turn may be connected to the network as described herein.

Remote networking device 4 may receive usage information 8 on demand, according to a schedule, or on an opportunistic basis. IMD 14 or patient programmer 26 may also transmit usage information 8 to remote networking device 4 when the respective memory is full. When receiving usage information 8 on demand, patient 12 or a clinician may initiate the transmission of usage information 8 to remote networking device 4. For example, patient 12 may interact with patient programmer 26, for example, by pressing one or more buttons on a keypad or selecting an item from a display of a graphical user interface, to send usage information 8 to remote networking device 4. In another example, a clinician may interact with a clinician programmer to send a request to IMD 14 or patient programmer 26 to retrieve usage information 8. In this example, the clinician may be located at a clinic or other remote location relative to patient 12 and the request may be sent via network 2.

In an example in which usage information 8 is received according to a schedule, IMD 14 or patient programmer 26 may store a schedule in local memory and send usage information 8 according to the schedule. Alternatively, remote networking device 4 may store a schedule in local memory and send a request to patient programmer 26 or IMD 14 to retrieve usage information 8 according to the schedule. In either case, the schedule specifies when usage information 8 is sent to remote networking device 4. The schedule may specify that usage information 8 is transmitted once per day, multiple times per day, once per week, multiple times per week, or at any other regular interval. The frequency at which usage information 8 is transmitted may depend on the size of memory of IMD 14 and patient programmer 26 and the amount of information recorded by IMD 14 and patient programmer 26.

Where remote networking device 4 receives usage information 8 on an opportunistic basis, IMD 14 and patient programmer 26 may transmit usage information 8 over network 2 whenever they are connected to network 2, e.g., within range of a link device that is connected to network 2. The link device may be a base station used for recharging patient programmer 26 that includes a connection to network 2, or any of the other link devices previously described in this disclosure.

It is also recognized that patient programmer 26 may have substantially permanent connection to network 2, such as a wireless connection. In such cases, patient programmer 26 may transmit usage information 8 to remote networking device 4 in real-time. That is, patient programmer 26 may transmit usage information 8 to remote networking device as usage information 8 is generated, or received from IMD 14 via telemetric communications.

Retrieving usage information 8 from patient programmer 26 or IMD 14 may also be performed through real-time interaction between patient 12 and a clinician. In this case, patient 12 and the clinician may communicate in real-time using patient programmer 26 and a clinician programmer, respectively. In this case, the clinician may use the clinician programmer to send a request to patient 12. Patient programmer 26 may prompt patient 12 in response to receiving the request. For example, patient programmer 26 may display a message that requires confirmation from patient 12 before sending usage information 8.

Remote networking device 4 may present usage information 8 to an authorized user, such as a clinician, a technician, or a manufacturer. For example, remote networking device 8 may present usage information to the user via a screen of a connected computing device, such as a clinician programmer, a desktop or laptop computer, workstation, PDA, or the like. In particular, remote networking device 4 may present usage information 8 as a graph, a chart, a diagram, a histogram, other graphical representation of information. With regards to usage information 8 that relates to use of therapy by patient 12, usage information 8 may be displayed as a histogram that illustrates percentages of a period of time that each program or group of programs was used to provide therapy at various times throughout the day, a diagram that illustrates when various parameter adjustments occurred, the parameters adjusted, and the adjusted parameter values, and a diagram that illustrates the overall usage of therapy during consecutive time periods. A clinician may use these diagrams to select programs for use in long term programming of IMD 14 or modify therapy parameters, programs, or program groups. A clinician may also use these diagrams to identify unexpected or undesirable therapy patterns, such as patient initiated therapy patterns that indicate drug seeking behavior or therapy patterns that indicate lack of use during a trial period or otherwise.

In addition or instead of presenting usage information 8, remote networking device 4 may analyze usage information 8 and suggest actions based on the analysis. For example, remote networking device 4 may analyze usage information 8 relating to the use of therapy by patient 12 and suggest therapy options or modifications to the therapy based on the analysis. In particular, remote networking device 4 may identify frequently used programs or program groups and suggest therapy options that are similar to the frequently used programs or groups. Remote networking device 4 may also suggest additional programs by frequently used programs or groups to programs tested on patient 12 during a programming session or a program library that stores a plurality of programs according to a set of hierarchical categories. Further, remote networking device 12 may also remove infrequently used programs or groups from a list of available programs or program groups.

Presenting a graphical representation of usage information 8 that relates to navigation patterns of the user interface of patient programmer 26 and use of features of patient programmer 26 may be useful to a manufacturer. Useful diagrams, graphs, and charts for the manufacturer may illustrate navigation patterns or relationships between navigation patterns used by patient 12, and the number of times different features of patient programmer 26 have been used by patient 12. By viewing the information, a manufacturer can provide more user friendly patient programmers to patients in future product developments by streamlining navigation patterns and including more of the frequently used features or providing easier access to frequently used features.

Figure 2:
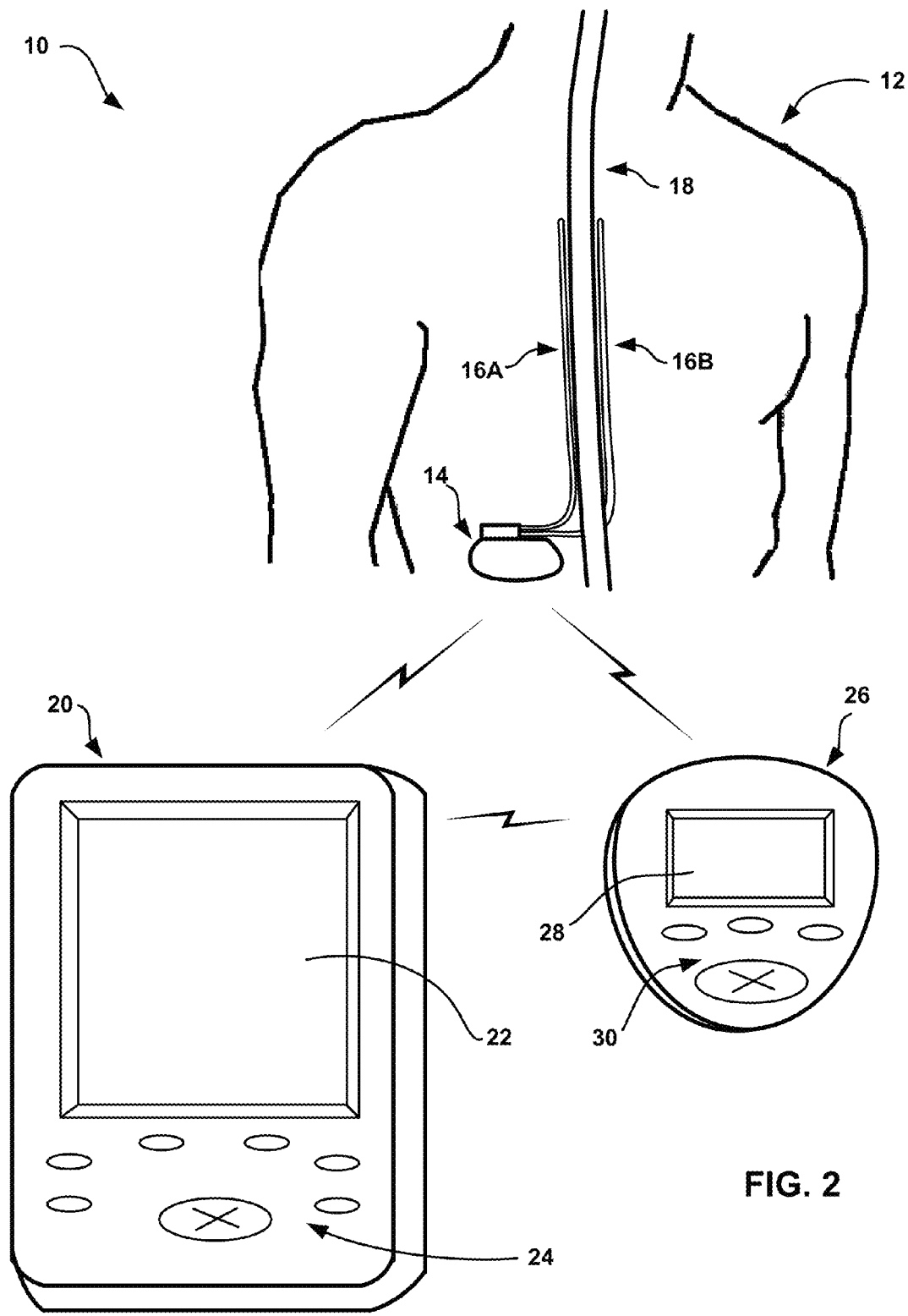
FIG. 2 is a conceptual diagram illustrating an example system for delivering therapy and programming delivery of therapy to the patient.

FIG. 2 is a diagram illustrating some components of system 10 in greater detail. In particular, FIG. 2 illustrates IMD 14, patient programmer 26, and clinician programmer 20 in greater detail. In FIG. 2, IMD 14 delivers neurostimulation therapy to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12. However, the invention is not limited to the configuration of leads 16 shown in FIG. 1 or the delivery of SCS therapy. For example, one or more leads 16 may extend from IMD 14 to the brain (not shown) of patient 12, and IMD 14 may deliver deep brain stimulation (DBS) therapy to patient 12 to, for example, treat tremor or epilepsy. As further examples, one or more leads 16 may be implanted proximate to the pelvic nerves (not shown) or stomach (not shown), and IMD 14 may deliver neurostimulation therapy to treat incontinence or gastroparesis. Further, IMD 14 may be a cardiac pacemaker, and leads 16 may extend to a heart (not shown) of patient 12.

As previously described with respect to FIG. 1, the invention is not limited to systems that include an implantable pulse generator, or even an IMD. For example, in some embodiments, a system according to the invention may include an implanted or external pump that delivers a drug or other agent to a patient via a catheter, e.g., for alleviation of pain by intrathecal drug delivery. Systems for delivering therapy to and programming delivery of a therapy for a patient according to the invention may include any type of implantable or external medical device.

IMD 14 delivers therapy according to program groups that each include at least one therapy program. Each program may include values for a number of parameters, and the parameter values define the therapy delivered according to that program. In embodiments where IMD 14 delivers neurostimulation therapy in the form of electrical pulses, the parameters may include voltage or current pulse amplitudes, pulse widths, pulse rates, and the like. Further, each of leads 16 includes electrodes (not shown in FIG. 2), and the parameters for a program may include information identifying which electrodes have been selected for delivery of pulses according to the program, and the polarities of the selected electrodes. In embodiments wherein IMD 14 delivers therapy via infusion of a drug or other agent, program parameters may include flow rates, agent types, concentrations, and infusion type, e.g., continuous or bolus.

Clinician programmer 20 may, as shown in FIG. 2, be a handheld computing device. Clinician programmer 20 includes a display 22, such as a LCD or LED display, to display usage information and other information to a user. Clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using a peripheral pointing devices, such as a stylus or mouse. Keypad 24 may take the form of an alphanumeric keypad or a reduced set of keys associated with particular functions. Display 22 may also present so-called soft keys for selection by the user.

Patient programmer 26, as shown in FIG. 2, may also be a handheld computing device. Patient programmer 26 includes a display 28 and a keypad 30, to allow patient 12 to interact with patient programmer 26. In some embodiments, display 26 may be a touch screen display, and patient 12 may interact with patient programmer 26 via display 28. Patient 12 may also interact with patient programmer 26 using peripheral pointing devices, such as a stylus or mouse. As previously described, patient 12 may use patient programmer 26 to control the delivery of neurostimulation therapy by IMD 14. For example, patient 12 may use patient programmer 26 to select the program or program group that will be used by IMD 14 to deliver therapy from one or more lists of programs or groups, adjust parameter values, and activate or deactivate therapy.

Clinician programmer 20 and patient programmer 26 are not limited to the handheld computing device embodiments shown in FIG. 2. Programmers 20, 26 may take the form of any type of computing device, such as desktop computers, laptop computers, or workstations coupled to a mainframe or other network resource.

Figure 3:
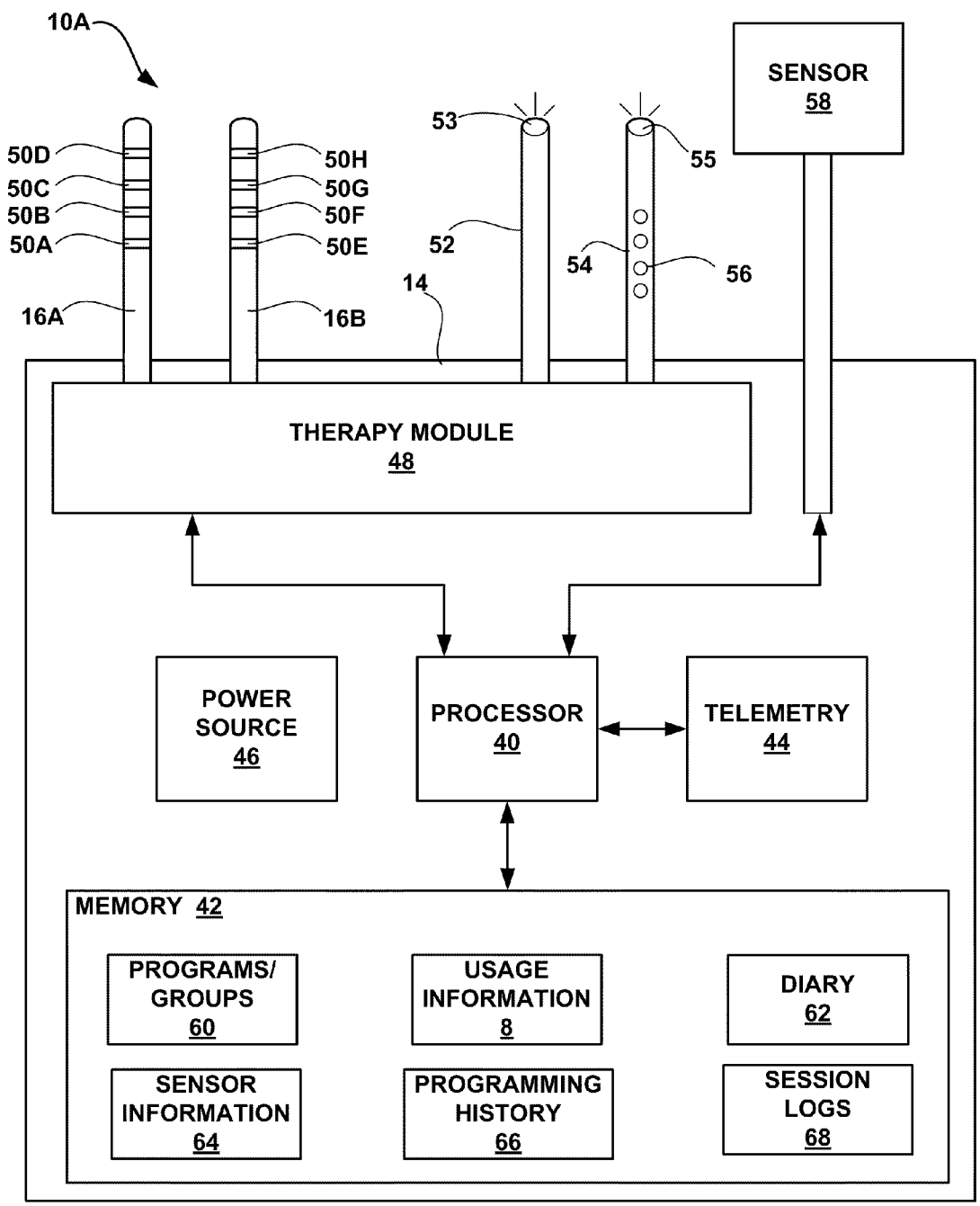
FIG. 3 is a block diagram illustrating an implantable medical device for delivering therapy to the patient according to one or more programs.

FIG. 3 is a block diagram illustrating an example configuration of IMD 14. IMD 14 may deliver neurostimulation therapy via electrodes 50A-D of lead 16A and electrodes 50E-H of lead 16B (collectively "electrodes 50"), drug therapy via fluid transfer devices 52 and 56, or both. Although illustrated in FIG. 3 as a single device that delivers one or both of neurostimulation therapy and drug therapy, separate devices may be used to deliver neurostimulation and drug therapy together or separately. That is, an implantable neurostimulator may be used to delivery neurostimulation therapy and a separate implantable drug pump may be used to delivery drug therapy. In this case, the implantable neurostimulator and implantable drug pump may be implanted at the same or different locations within patient 12.

Furthermore, in some embodiments, IMD 14 is configured to deliver only a single therapy, e.g., an IMD configured to deliver stimulation, an IMD configured to deliver only drug therapy, or an IMD configured to deliver some other therapy. Thus, FIG. 3 should not be considered limiting of the invention in any way. Instead, the purpose of FIG. 3 is to provide one example configuration of IMD 14.

In FIG. 3, IMD 14 is illustrated as having implantable leads 16 carrying electrodes 50 for delivering neurostimulation to patient 12 and fluid delivery devices 52 and 56 for delivering drug therapy. The configuration, type, and number of electrodes and fluid delivery devices in FIG. 3 are merely exemplary. Electrodes 50 may be ring electrodes or other types of electrodes such as cuff electrodes, paddle electrode leads, or segmented electrode arrays, e.g., arrays of electrodes disposed around a periphery of a lead.

Each fluid transfer device, e.g., a catheter, may have an elongated tubular body with an inner lumen. With reference to FIG. 3, the body may include a proximal opening to receive the drug and a distal opening 53, 55 for delivery of the drug to a target site. Additionally or alternatively, the elongated body may include a series of lateral outlets 56 formed in a lateral wall of the body that provide fluid communication between the inner lumen and the outside of the elongated body. Outlets 56 may be positioned at various axial positions along the length of the elongated body, as well as various circumferential positions. Lateral outlets 56 may be concentrated towards a distal end of the fluid delivery device.

Therapy module 48 may include an implantable stimulation generator or other stimulation circuitry, e.g., capacitive elements and switches that delivers electrical signals to patient 10 via at least some of electrodes 50 under the control of processor 40. Additionally or alternatively, therapy module 48 may include one or more fluid reservoirs and one or more pump units that pump fluid from the fluid reservoirs to the target site through fluid transfer devices 52 and 54. The fluid reservoirs may contain a drug or mixture of drugs. The fluid reservoirs may provide access for filling, e.g., by percutaneous injection of fluid via a self-sealing injection port. Fluid delivery devices 52 and 54 may comprise, for example, catheters that deliver, i.e., infuse or disperse, drugs from the fluid reservoirs to the same or different target sites within patient 12.

Processor 40 controls therapy module 48 to deliver neurostimulation therapy and drug therapy according to one or more selected programs. Where IMD 14 delivers neurostimulation therapy, processor 40 may control therapy module 48 to delivery electrical pulses with the amplitudes and widths, and at the rates specified by the one or more selected programs. Processor 40 may also control therapy module to deliver the pulses via a selected subset of electrodes 50 with selected polarities, as specified by the selected programs. Where a plurality of programs are selected at a given time, processor 40 may control therapy module 48 to delivery each pulse according to a different one of the selected programs. In embodiments in which IMD 14 delivers drug therapy to patient 12, processor 40 may control which drugs are delivered and the dosage of the drugs delivered. Processor 40 may take the form of microprocessors, digital signal processors (DSPs), application specific integrated circuits (ASICs), field-programmable gate arrays (FPGAs), other discrete or integrated logic circuitry, or any combination of such components.

IMD 14 also includes a memory 42. Memory 42 stores programs or program groups 60 that are available to be selected by patient 12 for delivery of therapy, and stores usage information 8 recorded by processor 40. As described in this disclosure, usage information 8 may include information that relates to use of therapy by patient 12, i.e., information relating to the use of programs/groups 60 by patient 12, adjustments to programs or groups by patient 12, and the overall use of therapy by patient 12. For example, usage information 8 for a program may indicate the number of times patient 12 selected a program, the average or median length of time that a program was used when selected, the average amount of time a program was used over a period of time, such as one a per day, week, or month basis, or the total amount of time or percentage of time that the program was used since the most recent programming session. Usage information 8 may also include information that relates to navigation patterns of a user interface of patient programmer 26, or information that relates to use of features of patient programmer 26.

IMD 14 also includes a telemetry circuit 44 that allows processor 40 to communicate with clinician programmer 20 and patient programmer 26. Processor 40 may receive programs to test on patient 12 from clinician programmer 20 via telemetry circuit 44 during a programming session. Where IMD 14 stores programs 60 in memory 42 for long-term use, processor 40 may receive programs 60 from clinician programmer 20 via telemetry circuit 44, e.g., at the end of a programming session, and later receive program selections made by patient 12 from patient programmer 26 via telemetry circuit 44. Where patient programmer 26 stores the programs, processor 40 may receive programs selected by patient 12 from patient programmer 26 via telemetry circuit 44.

Telemetry circuit 44 also allows processor 40 to communicate with remote networking device 4. Specifically, telemetry circuit 44 allows processor 40 to connect to network 2 for transmitting usage information 8 to remote networking device 4. Processor 40 may transmit usage information 8 to remote networking device 4 via telemetry circuit 44 in response to receiving a request from remote networking device 4. Alternatively, processor 40 may automatically transmit usage information 8 to remote networking device 4 via telemetry circuit 44 in accordance with a schedule, on an opportunistic basis, or based on memory capacity.

In some embodiments, processor 40 receives patient diary information 62 entered by patient 12 using patient programmer 26 via telemetry circuit 44, and stores the diary information within memory 42. Diary information 62 may include textual or numerical comments or ratings regarding efficacy, side-effects, use, or the like of programs, recorded by patient 12 outside of a clinic. Clinician programmer 20 and remote networking device 4 may, in some embodiments, retrieve diary information 51 from memory 42 via telemetry circuit 44.

Further, in some embodiments, clinician programmer 20 stores a programming history 66 and session logs 68 within memory 42 of IMD 14, and may retrieve the programming history and session logs from memory 42, via telemetry circuit 44. Remote networking device may also, in some embodiments, retrieve the programming history and session logs from memory 42 via telemetry circuit 44. Programming history 66 and session logs 68 may include a record of programs tested during one or more prior programming sessions and information for the program, e.g., combinations of therapy parameters, information describing the parameters and rating information for the program, and clinician comments regarding the program. Programming history 66 may include selected programs from each of session logs 68. For example, programming history 66 may include only information regarding programs that were programmed into IMD 14 for long-term delivery of therapy at the end of a programming session, rather than all of the programs tested during the programming session. In this respect, programming history 66 may act as a summary for session logs 68. Accordingly, clinician programmer 20 may access programming history 66 and session logs 68 in order to provide programming guidance information to a user during a programming session.

Memory 42 may also include program instructions that, when executed by processor 40, cause processor 40 and IMD 14 to perform the functions ascribed to IMD 14 herein. Memory 42 may include any volatile, non-volatile, fixed, removable, magnetic, optical, or electrical media, such as a RAM, ROM, NVRAM, EEPROM, flash memory, and the like.

Additionally, as illustrated in FIG. 3, IMD 14 may include one or more physiological sensors 58 that generate signals as a function of a physiological parameter of patient 12. For example, physiological sensors 58 may include accelerometers or other sensors that generate signals as a function of patient activity, gait or posture. As other examples, physiological sensors 58 may include electrodes that detect an electromyogram (EMG), electrocardiogram (ECG), electroencephalogram (EEG), or impedance-based respiration of patient 12. Further, physiological sensors 58 may include known transducers that generate a signal based on a blood pressure or blood oxygen saturation of patient 12. Although illustrated in FIG. 3 as being coupled to IMD 14 via a lead, sensors 48 may be located within IMD 14 or wirelessly coupled to IMD 14.

Accordingly, processor 40 may store sensor information 64 in memory 42 based on the signals generated by sensors 58. The physiological parameters detected by sensors 58 and, therefore, sensor information 64, may reflect the severity or prevalence of pain, movement disorders, epilepsy, mood disorders, cardiac disorders, gastrointestinal or urinary disorders, or side-effects associated with the treatment of such symptoms or disorders. In some embodiments, processor 40 may associate sensor information 64 with the one or more of programs 60 presently used by therapy module 48 for delivery of therapy. In this manner, sensor information 64 may advantageously provide objective information regarding the efficacy or side-effects associated with delivery of therapy according to the programs. In some embodiments, processor 40 may store sensor information 64 in association with the programs within the programming history 66, or may provide the sensor information to clinician programmer 20 for inclusion in a programming history. Clinician programmer 20 and/or remote networking device 4 may retrieve sensor information via telemetry circuitry 44.

Sensor information 64 may include raw data derived from the signals output by the sensors, averages or other statistical representations of such data, or any other metric derived from such data. For example, in embodiments in which sensors 58 include one or more accelerometers or EMG electrodes, processor 40 may periodically detect the severity of tremor, or may detect incidences where patient 12 falls or experiences immobility, e.g., a gait freeze. Processor 40 may record the information describing the severity of the tremor and times of detection, or numbers and times of falls or immobility, as sensor information 64. These examples of sensor information 64 may be particularly relevant as, for example, an objective indication of the efficacy of a movement disorder treatment program, e.g., a deep brain stimulation program.

The illustrated components of IMD 14 receive energy from a power source 46, such as a battery or other suitable power source. Power source 46 may take the form of a small, rechargeable or non-rechargeable battery, or an inductive power interface that transcutaneously receives inductively coupled energy. In the case of a rechargeable power source of an implanted device, the power source may include an inductive power interface for transcutaneous transfer of recharge power to the IMD power source.

Figure 4:
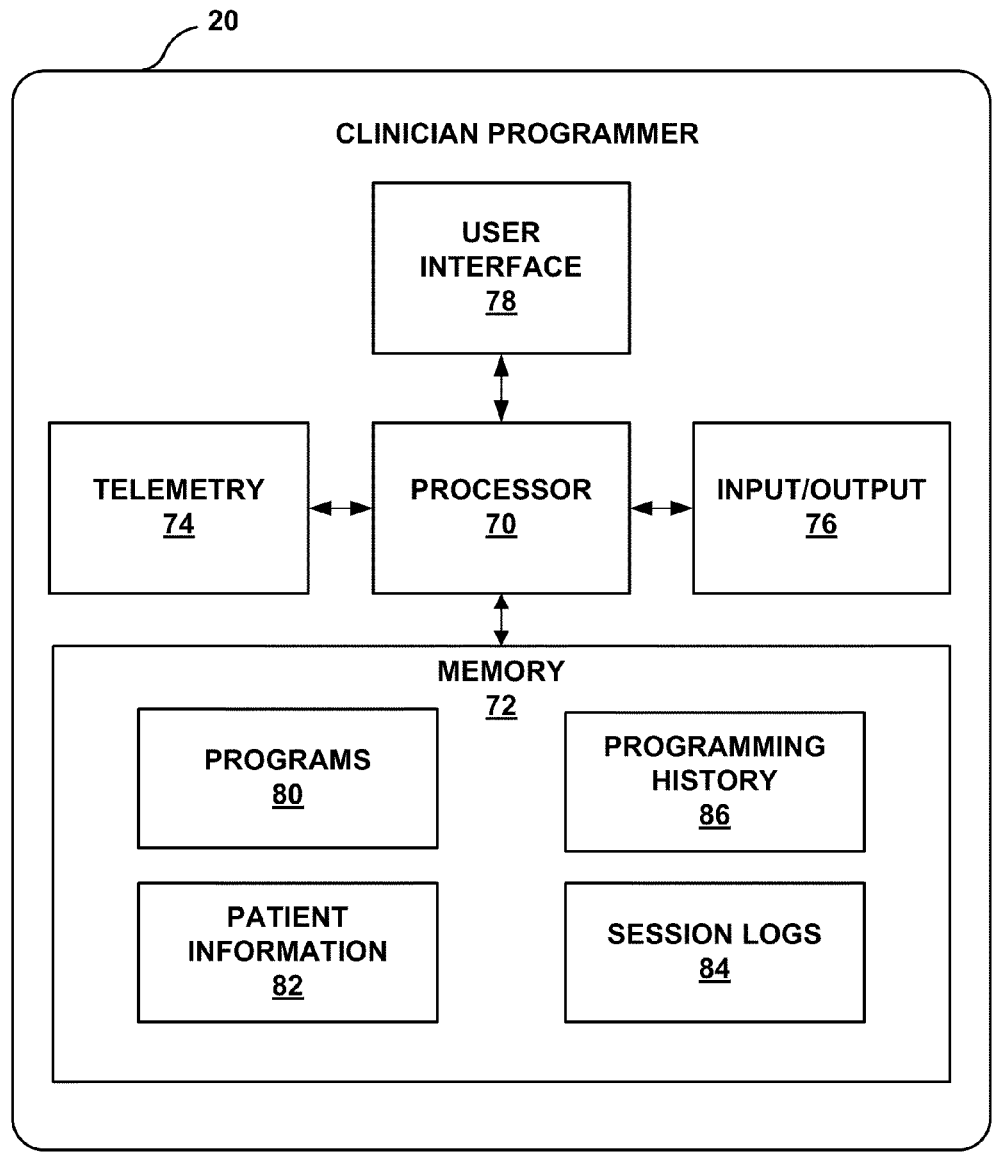
FIG. 4 is a block diagram illustrating an example clinician programmer that allows a clinician to control delivery of therapy by the implantable medical device and collects usage information.

FIG. 4 is a block diagram illustrating an example configuration of clinician programmer 20. A clinician may interact with a processor 70 via a user interface 78 to program therapy for patient 12 as described herein. User interface 78 may include display 22 and keypad 24, and may also include a touch screen or peripheral pointing devices as described above. Processor 70 may also provide a graphical user interface (GUI) via display 22 to facilitate interaction with a clinician. Processor 70 may include a microprocessor, a controller, a DSP, an ASIC, an FPGA, discrete logic circuitry, or the like.

Clinician programmer 20 also includes a memory 72. Memory 72 may include program instructions that, when executed by processor 70, cause clinician programmer 20 to perform the functions ascribed to clinician programmer 20 herein. Memory 72 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

A clinician may program therapy for patient 12 by specifying programs to test on patient 12 during a therapy programming session. The clinician may interact with the GUI and user interface 78 in order to specify programs to IMD 14 for delivery to patient 12 via telemetry circuit 74.

Processor 70 may store the specified programs 80 within memory 72, and transmit specified programs 80 to IMD 14 via telemetry circuit 74 or to patient programmer 26 via input/output (I/O) circuitry 76. In this manner, processor 70 may be used to control IMD 14 to delivery therapy for purposes of evaluating effectiveness of particular programs. I/O circuitry 76 may include transceivers for wireless communication, appropriate ports for wired communication or communication via removable electrical media, or appropriate drives for communication via removable magnetic or optical media.

Processor 70 may maintain a session log 84 for patient 12 during programming of therapy for patient 12 by the clinician. Upon delivery of a selected or specified program, the clinician or patient 12 may enter rating information relation to the tested program via the GUI and user interface 78. Processor 70 may store information identifying tested programs and associated rating information as part of session log 84. Information identifying tested programs may include the parameters for the tested programs. Processor 70 may present a listing of tested programs and associated rating information to the clinician in order to facilitate selection of programs for programming IMD 14.

Processor 70 may also maintain a programming history 86 for patient 12, which may take the form of a record of programs, e.g., combinations of therapy parameters tested during one or more prior programming sessions. During an initial programming session, processor 70 may create the programming history by storing all or selected ones of the programs within the session log 84 for that session within programming history 86. Similarly, processor 70 may include all or selected ones of the programs from the session logs 84 for follow-up programming sessions within the programming history 86 for patient 12, or may update the programming history 86 based on retesting of programs during a follow-up programming session. The programming history may include the information stored for a program in the session log 84, e.g., information describing the parameters and rating information for the program, and may include clinician comments regarding the program. The rating information may rate a program in terms of therapeutic efficacy, side effects, IMD power consumption associated with delivery of therapy according to the program, or the like.

In some embodiments, during a current programming session, processor 70 may retrieve usage information 8, diary information 62, and sensor information 64 from IMD 14 or patient programmer 26, and may update the record for those programs within the programming history 86 to include the usage, diary and sensor information. Processor 70 may display the programming history 86 to the clinician during the current programming session via the GUI provided by user interface 78, and the display of programming history 86 may assist the clinician in more quickly identifying desirable programs during the current programming session. Processor 70 may receive selection of a particular field within the programming history 86, e.g., rating information related to effectiveness or side effects, via user interface 78, and may order the display of the programming history 86 via the GUI according to the selected field. Further, processor 70 may analyze, or otherwise use the programming history 86 to provide guidance information to a user, such as a clinician, via user interface 78. The guidance information may assist the user in more quickly identifying one or more desirable programs during the current programming session. Additionally, in embodiments in which the programming history 86 and session logs 84 for patient 12 include different information or different quantities of information, clinician programmer 20 may access historical session logs 84 as necessary during a programming session for presentation to a clinician or formulation of guidance information.

Although illustrated in FIG. 4 as stored within memory 72 that is within clinician programmer 20, programming histories 86 need not be stored within a fixed memory of the clinician programmer. Memory 72 may include removable media on which programming histories 86 may be stored, or programming histories 86 may be stored within a memory of another computing device accessible to processor 70, e.g., remote networking device 4 via a network 2. Further, processor 70 may store the programming histories for patient 12 within memory 42 of IMD 14 or memory of patient programmer 26, and may retrieve the programming histories, including usage, sensor and diary information, from the IMD or patient programmer.

The clinician may interact with the GUI and user interface 78 to collect a variety of additional types of information during a programming session. For example, the clinician may enter patient information 82, including age, height, weight, sex, and symptoms. As another example, the clinician may enter device configuration information (not shown), including a device type of IMD 14, a number and type of leads 16, a number of electrodes, the configuration of the electrodes, e.g., their position within the body, a number of fluid transfer devices, and drugs delivered by the fluid transfer devices. Patient information 82 and device configuration information may be stored within memory 72, and, in some embodiments, may be transmitted via I/O circuitry 76 to a remote computing device such as remote networking device 4 or other database coupled to clinician programmer 20 via a network.

Figure 5:
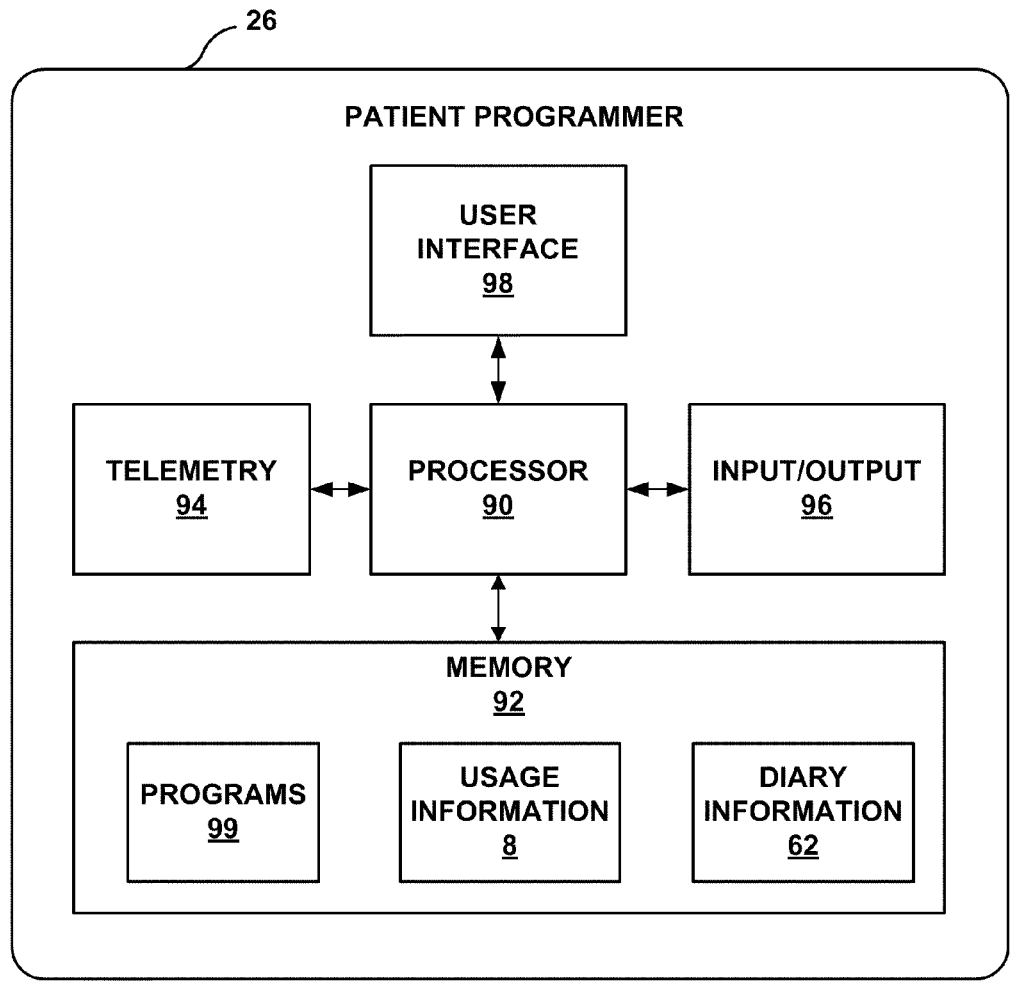
FIG. 5 is a block diagram illustrating an example patient programmer that allows a patient to control delivery of therapy by the IMD, collects usage information, and interacts with the remote networking device.

FIG. 5 is a block diagram illustrating an example configuration of patient programmer 26. Patient 12 may interact with a processor 90 via a user interface 98 in order to control delivery of neurostimulation therapy by, for example, starting and stopping delivery of therapy, adjusting parameters of programs, and selecting from among a plurality of available programs. User interface 98 may include display 28 and keypad 30, and may also include a touch screen or peripheral pointing devices as described above. Processor 90 may also provide a graphical user interface (GUI) via display 28 to facilitate interaction with patient 12. Processor 90 may include a microprocessor, a controller, a DSP, an ASIC, an FPGA, discrete logic circuitry, or the like.

Patient programmer 26 also includes a memory 92. In some embodiments, memory 92 may store a plurality of programs 99 that are available to be selected by patient 12 for delivery of therapy. A program selected by patient 12 is delivered to IMD 14 via telemetry circuit 92, and used by IMD 14 to control delivery of therapy by IMD 14. Between clinic visits, processor 90 may record usage information 8 and diary information 62 entered by patient 12 via user interface 98. Processor 90 stores the usage and diary information in memory 92.

As previously described, usage information 8 includes information that relates to the use of system 10 by patient 12, i.e., information that relates to use of therapy by patient 12, information that relates to navigation patterns of a user interface of patient programmer 26, and information that relates to use of features of patient programmer 26.

Memory 92 may also include program instructions that, when executed by processor 90, cause patient programmer 26 to perform the functions ascribed to patient programmer 26 herein. Memory 92 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Patient programmer 26 also includes a telemetry circuit 94 that allows processor 90 to communicate with IMD 14 and input/output (I/O) circuitry 96 that allows processor 90 to communicate with clinician programmer 20. Processor 90 may receive program selections made by patient 12 via user interface 98, and may transmit either the selection or the selected program to IMD 14 via telemetry circuitry 94 for delivery of therapy according to the selected program.

Where patient programmer 26 stores programs 99 in memory 92, processor 90 may receive programs 99 from clinician programmer 20 via input/output circuitry 96 that were selected for long-term use as a result of a programming session. Processor 90 may also provide usage information 8 and other information, such as diary information (not shown in FIG. 5) to clinician programmer 20 via I/O circuitry 96. I/O circuitry 96 may include transceivers for wireless communication, appropriate ports for wired communication or communication via removable electrical media, or appropriate drives for communication via removable magnetic or optical media.

Figure 6:
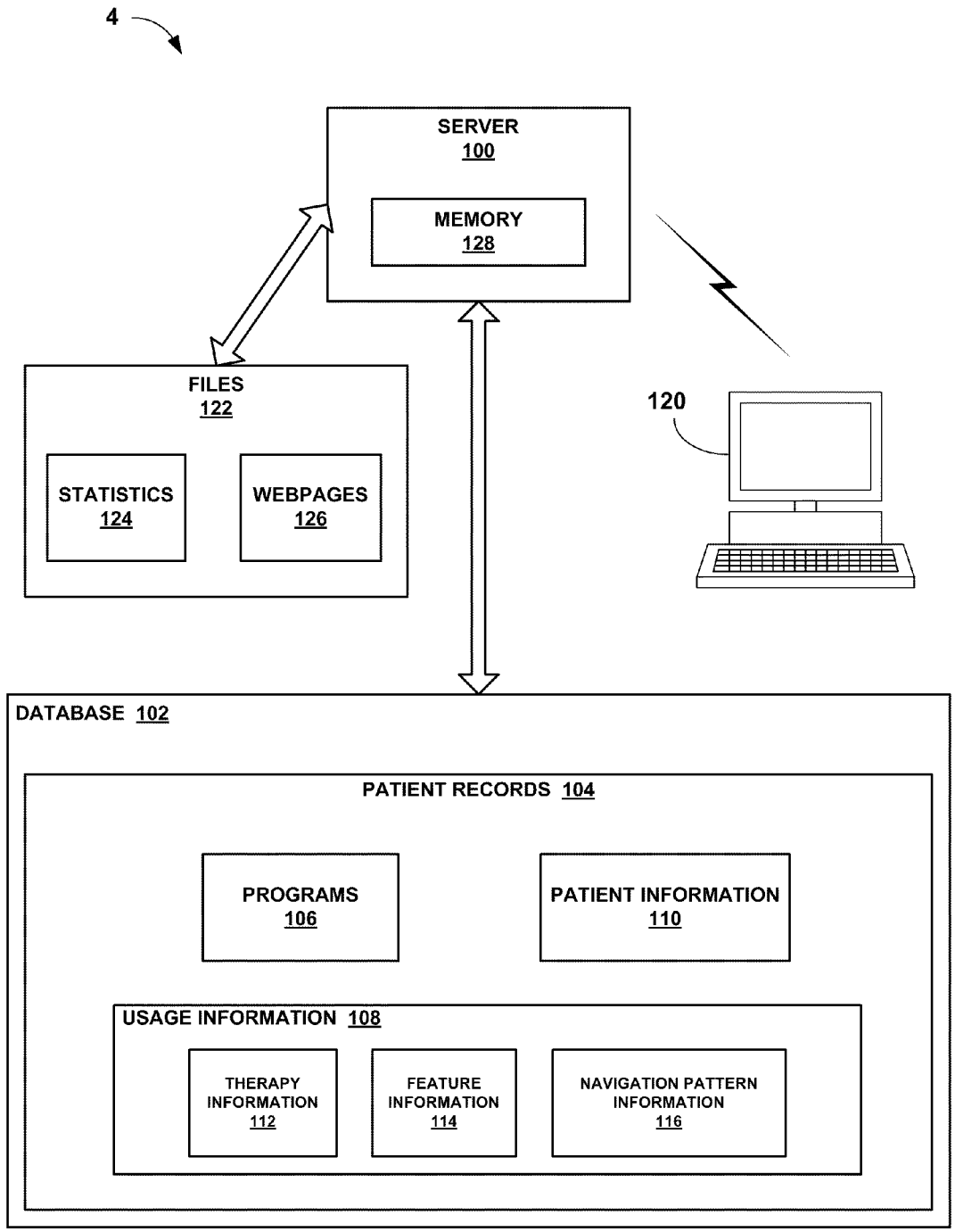
FIG. 6 is a block diagram illustrating the system in FIG. 1 in greater detail.

FIG. 6 is a block diagram illustrating remote networking device 4 according to one example embodiment. In FIG. 6, remote networking device includes a server 100 that interacts with IMD 14, patient programmer 26, and clinician programmer 20 via network 2 (not shown in FIG. 6) as previously described in this disclosure. Server 100 accesses database 102 that stores programs and information as patient records 104 for a plurality of patients, i.e., patient 12 and one or more other patients.

Patient records 104 for a patient 12 may include selected programs 106, usage information 108, and patient information 110 for the patient. In FIG. 6, usage information 108 includes therapy information 122 that relates to use of therapy by a patient, feature information 114 that relates to use of features of patient programmer 26, and navigation pattern information 116 that relates to navigation patterns of a user interface of patient programmer 26. Because patient records 104 store programs and information for a plurality of patients, usage information 108 includes usage information 8 (FIGS. 3-5) and usage information for other patients. Similarly, programs 106 may include programs 60 (FIG. 3), programs 80 (FIG. 4), programs 99 (FIG. 5) and programs associated with other patients, and patient information 110 includes patient information 82 and patient information associated with other patients. Although not shown in FIG. 6, patient records 104 may also include other information associated with a patient, such as sensor information, diary information, programming history, and session logs.

As described above, server 100 receives usage information from IMD 14 or patient programmer 26 and accesses database 102 to record the received information as usage information 108 in patient records 104. Server 100 creates files 122 based on the received usage information and serves the created files to clinician programmer 20 (not shown) or another computing device 120. Computing device 120 may be used to interact with server 100 according to some embodiments of the invention. Computing device 120 may be a laptop or desktop computer, a workstation, a PDA, or the like. Moreover, in some embodiments, more than one computing device, each of which may be located in a different location, may be used to interact with server 100 thereby enabling a plurality of clinicians at different locations to access, review, and/or analyze patient records 104 at some time after the respective programming sessions for those patients. Computing device 120 and server 100 may communicate with each other via network 2 (not shown in FIG. 6). Thus, computing device 120 may be located in a clinical environment that is remotely located from server 100, which may be located at a remote computing facility. Furthermore, as discussed above, in various embodiments clinician programmers 20 may take the form of any type of computing device, such as a laptop or desktop computer, a workstation, a PDA, or the like.

For example, statistics 124 relating to usage information may be compiled and presented to clinicians as files 122 via clinician programmer 20 or computing device 120. Files 122 may take the form of webpages 126 served to clinician programmer 20 or computing device 120 by server 100. In any case, files 122 may generally present a graphical representation of usage information 108, such as diagram, a chart, or a graph. Using therapy information 112 as an example, files 122 may present therapy information 112 as a histogram that illustrates percentages of a period of time that each program or program group was used to provide therapy at various times throughout the day, a diagram that illustrates when various parameter adjustments occurred, the parameters adjusted, and the adjusted parameter values, and a diagram that illustrates the overall usage of therapy by patient 12. Where feature information 114 is used as an example, files 122 may present feature information 114 as a graph that illustrates the number of times each feature was used. As another example, files 122 may present navigation pattern information 116 as a diagram that illustrates frequently used navigation patterns or a graph that illustrates the number of times different navigation patterns were used. These examples should not be considered limiting of the invention as broadly described in this disclosure. Rather, it should be recognized that these are merely a few of many diagrams, charts, graphs, and histograms that may be presented to a clinician or other authorized user, such as a technician or manufacturer of IMDs or programmers.

In some embodiments, server 100 or a human administrator, such as a clinician, a technician, a manufacturer, or other authorized person, may analyze usage information 108 and suggest one or more actions based on the analysis. Server 100 may, for example, analyze the received information usage information according to a set of rules or guidelines or by comparison to information within database 102. A human administrator may analyze usage information 108 using one or more of the graphs, charts, diagrams, or histograms generated by server 100. For example, server 100 or a human administrator may analyze therapy information 112 and suggest therapy options or modifications to the therapy based on the analysis, e.g., suggest therapy options that are similar to frequency used programs or program groups, suggest additional programs or groups based on frequently used programs or groups, or remove programs or groups that are used infrequently from the list of available programs or groups. As another example, server 100 or a human administrator may analyze feature information 114 and navigation pattern information 116 to develop more user friendly patient programmers in future product developments.

In other example embodiments, server 100 may analyze usage information 108 and control the status of patient programmer 26 based on the analysis. As previously described, server 100 may analyze usage information 8 to identify unwanted and/or unexpected therapy patterns, such as drug seeking behavior. Upon identifying an unwanted therapy pattern, server 100 may send a control signal to patient programmer 26 via network 2 that causes programmer 26 to operate in a locked state that prevents patient 12 from programming IMD 14 or using other features of programmer 26, i.e., to prevent the patient from furthering such behavior. Server 100 may also suggest to patient 12 to contact a clinician or visit a clinic to remove the locked state by, for example, sending information to patient programmer 26 which programmer 26 displays on a screen to patient 12. Programmer 26 may also provide various other alerts such as audible or tactile alerts. In addition to or as an alternative to alerting patient 12, server 100 may alert a clinician, technician or other authorized user that patient programmer 26 is operating in a locked state. Server 100 may alert an authorized user by displaying a message on a monitor or screen of an associated computing device, generating an audible alert, or the like.

Other examples of unwanted and/or unexpected therapy patterns that may be identified by server 100 or a user of the server include failure to use certain programs groups stored in the IMD or patient programmer, particularly during a period in which the patient is expected to trial or sample a variety of groups, unusually low or high values for certain therapy parameters, such as amplitude, or general failure to activate therapy. Such therapy patterns may indicate lack of experience with or understanding of the features of system 10 and the therapy provided by IMD 14, dissatisfaction with the therapy, or ineffective therapy. In some example embodiments, server 100 may suggest action or provide guidance to patient for proper use of system 10.

In some embodiments, server 100 may identify an unexpected change in therapy, such as an abrupt or drastic change in an establish usage pattern, e.g., reflective of a typical or prescribed therapy sequence for patient 12. Such a change may be indicative of patient error in changing a program or parameter, a significant change in patient symptoms, or any other of a variety of issues. In some embodiments, server 100 may alert an authorized user in response to identifying such a change or perform any other appropriate response.

In any case, server 100 may produce a result, such as a suggested program, adjustment to a program or therapy, programming guidance, maintenance instructions, and the like, based on the analysis. The result is transmitted to the appropriate programming or computing device, such as patient programmer 26, and may be used to improve operation of system 10.

System 10 allows a clinician, technician, or manufacturer to view and analyze programs and information, e.g., usage information, from any computing device capable of accessing server 100 via network 2, such as clinician programmer 20 and computing device 120. Allowing a human administrator greater access to programs and information may lead to more effective and efficient therapy and use of clinician time. In particular, IMD 14 or patient programmer 26 may transmit information regarding usage information through a network connection in a home environment without requiring patient 12 to visit a specialized clinic. Further, a clinician may be able to access usage information without personal clinician/patient interact. For example, either of IMD 14 and patient programmer 26 may transmit usage information to server 100 via network 2 on a periodic basis, e.g., according to a schedule stored in a local memory, or on demand, e.g., in response to receiving a clinician initiated request from server 100 or clinician programmer 2. Database 102 stores the information as part of a patient record 104 for patient 12 that may be accessed by a human administrator via a computing device capable of accessing server 100, such as clinician programmer 20, computing device 120, or similar computing device.

Patients may be provided a level of access to server 100 via patient programmer 26 or associated programming device, such as a personal laptop or desktop computer executing IMD programming software, for review of their patient record 104 or to view statistics 124 or webpages 126. As another example, the information stored within database 102 and statistics 124 may be available for analysis by academic or corporate researchers using a computing device 120. Levels of access to database 102 and files 122 via server 100 may be controller by server 100 based on user profiles established by an administrator and stored in memory 128.

FIGS. 7, 8, 9A and 9B illustrate example diagrams that may be presented to a human administrator by clinician programmer 20 or computing device 120 via graphical user interface (GUI) 130. The invention is not limited to illustrated forms of presenting usage information. Rather, it should be understood that a variety of diagrams, histograms, charts, graphs, summaries, or the like may be used to present usage information, e.g., information that relates to use of therapy by patient 12, information that relates to use of features or patient programmer 26, information that relates to use of navigation patterns of a user interface of patient programmer 26, and information that relates to performance of IMD 14 or patient programmer 26, to a human administrator. As an example, clinician programmer 20 or computing device 120 may present a trend graph or the like illustrating the value of a program parameter, such as amplitude, over time.

Figure 7:
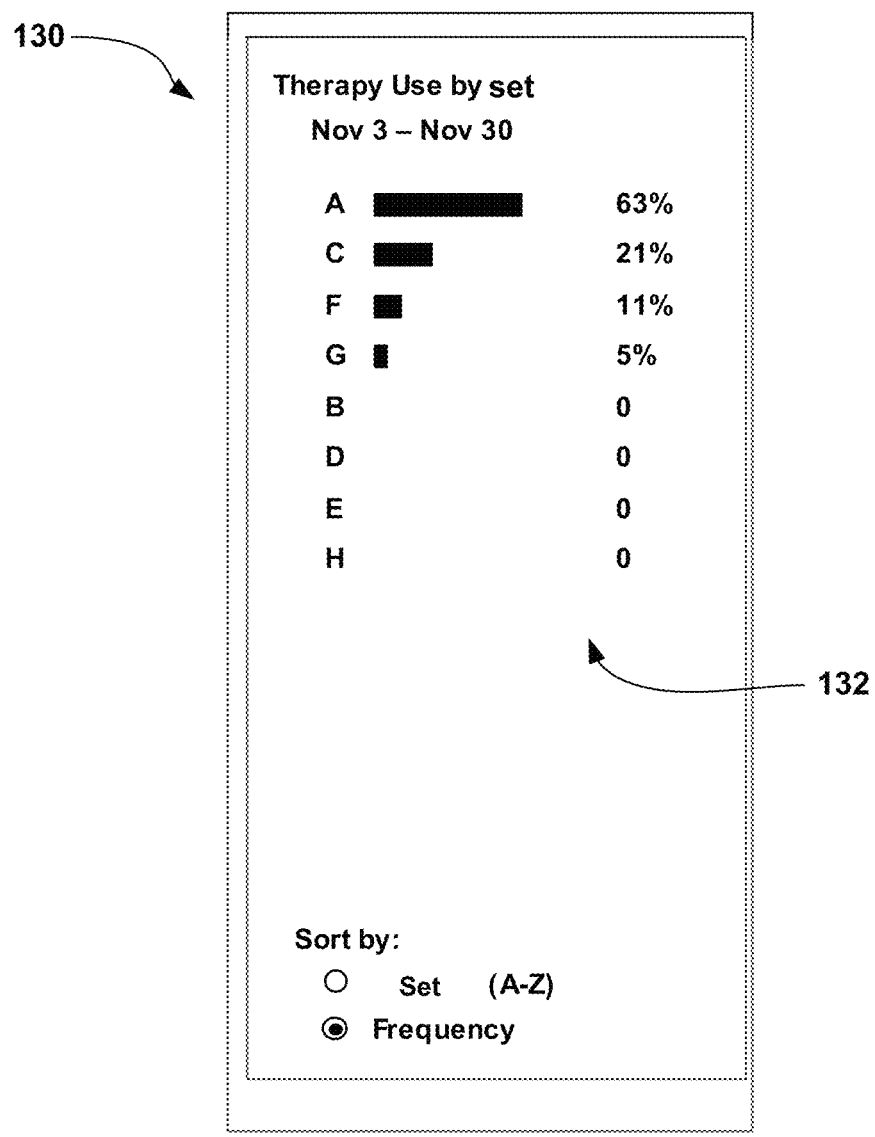
FIGS. 7, 8, 9A, and 9B are diagrams illustrating example graphical user interfaces that may be provided by a clinician programmer to present usage information to a clinician.

As shown in FIG. 7, clinician programmer 20 or computing device 120 may present a histogram 132 that illustrates percentages of the total therapy use for each of a plurality of program groups. Histogram 132 may be used by the clinician to determine which program groups were preferred or effective, and which program groups were not preferred or ineffective. The clinician may eliminate unused program groups, and add additional program groups that are similar to the preferred or effective program groups. Clinician programmer 20 may mark unused program groups for removal from a list. A similar histogram may be used to illustrate percentages of the total therapy use for individual programs.

Figure 8:
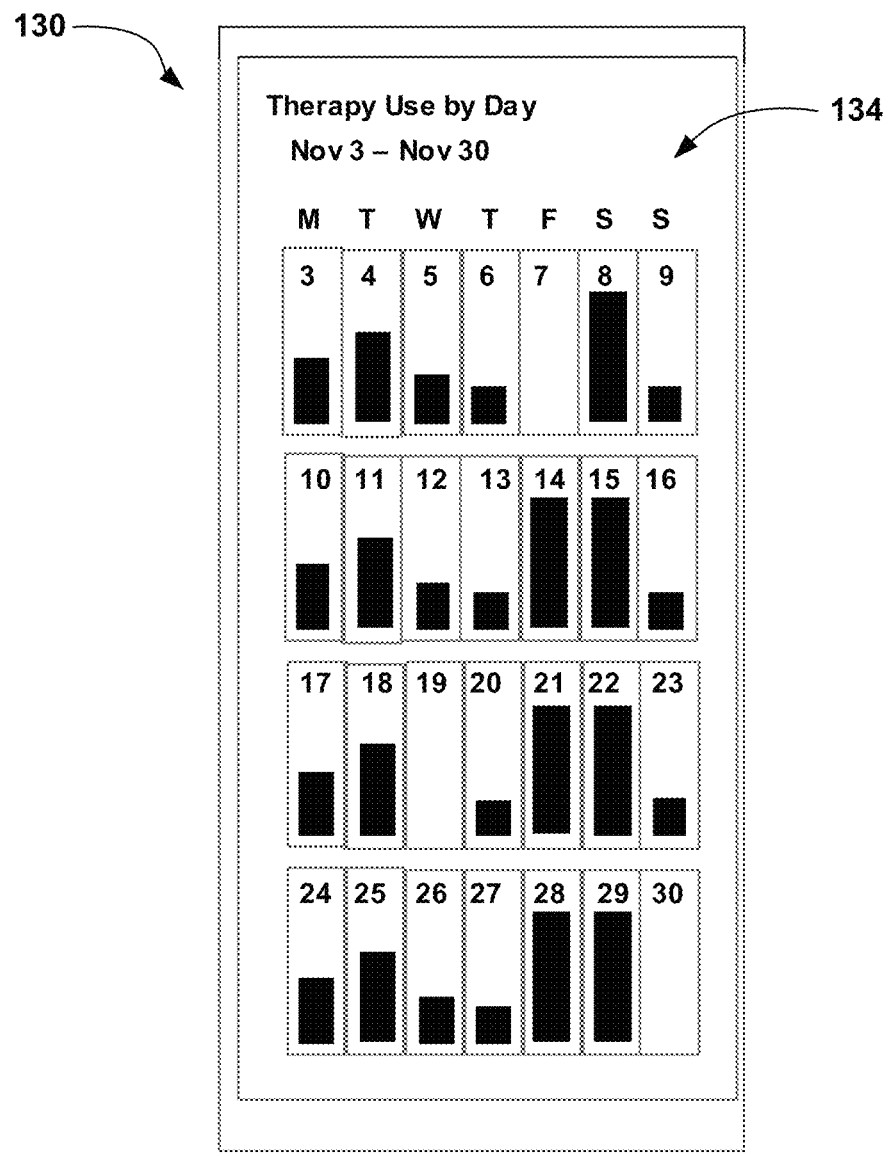

FIG. 8 illustrates a calendar-view diagram 134 that may be presented by clinician programmer 20 or computing device 120. Diagram 134 illustrates overall therapy usage each day, and may be used by the clinician to evaluate day-to-day changes in the symptoms of patient 12. Similar diagrams may be used to illustrate month-to-month, or week-to-week changes in therapy usage. Trends in the data illustrated by diagram 134 may suggest a need to provide new programs or program groups to address changes in symptoms of patient 12.

Figure 9A:
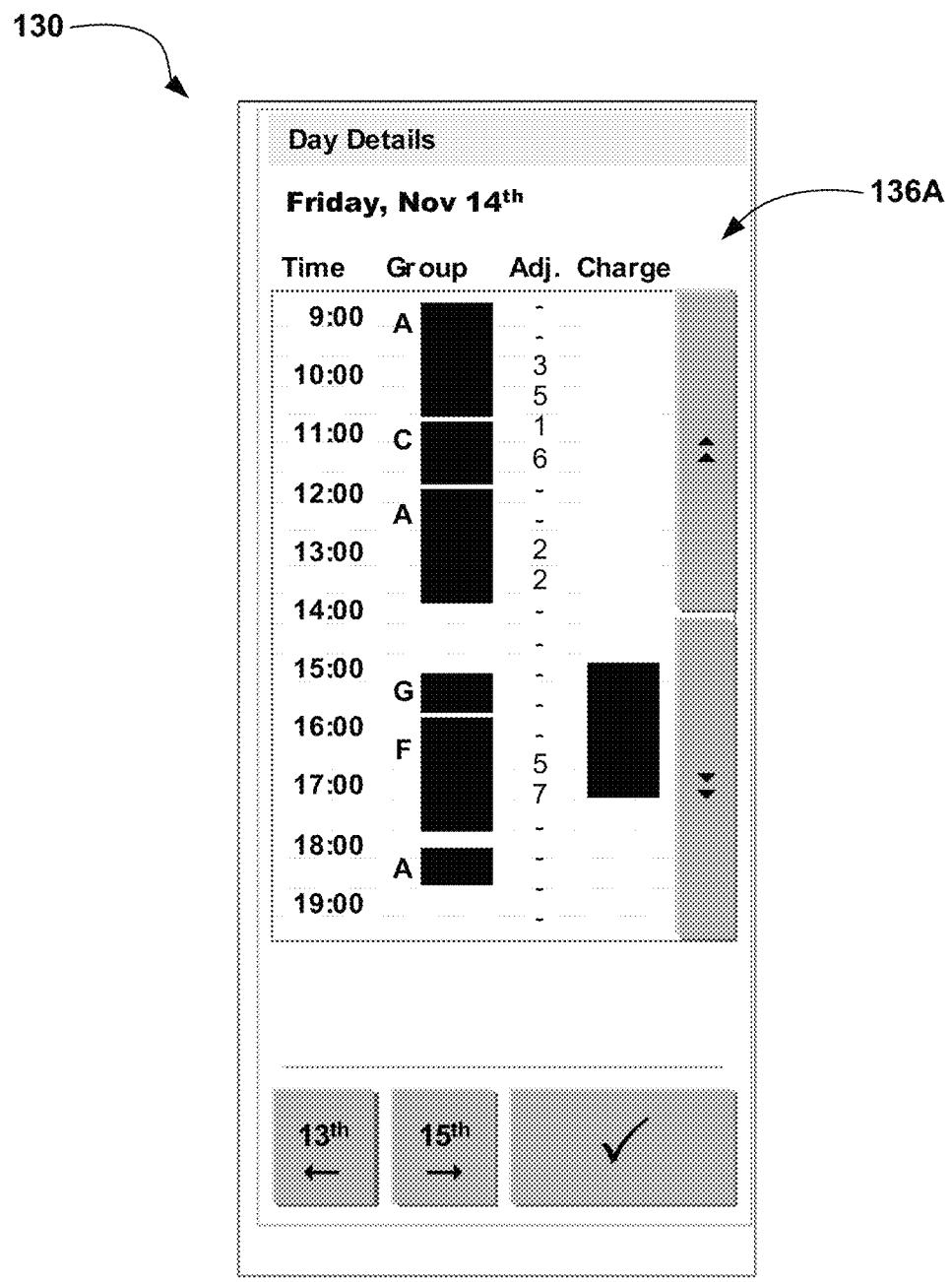

FIG. 9A illustrates a day-view diagram 136A that may be presented by clinician programmer 20. For a selected day, diagram 136A illustrates which, if any, program group was activated at any given time. Diagram 136A also illustrates the time of adjustments to program groups made during the day. Diagram 136A may be used by the clinician to evaluate cyclical changes in the activity or symptoms of patient 12 throughout a day. Trends in the data illustrated by diagram 136A may suggest a particular activity or time of day for which new programs or groups would be beneficial.

Figure 9B:
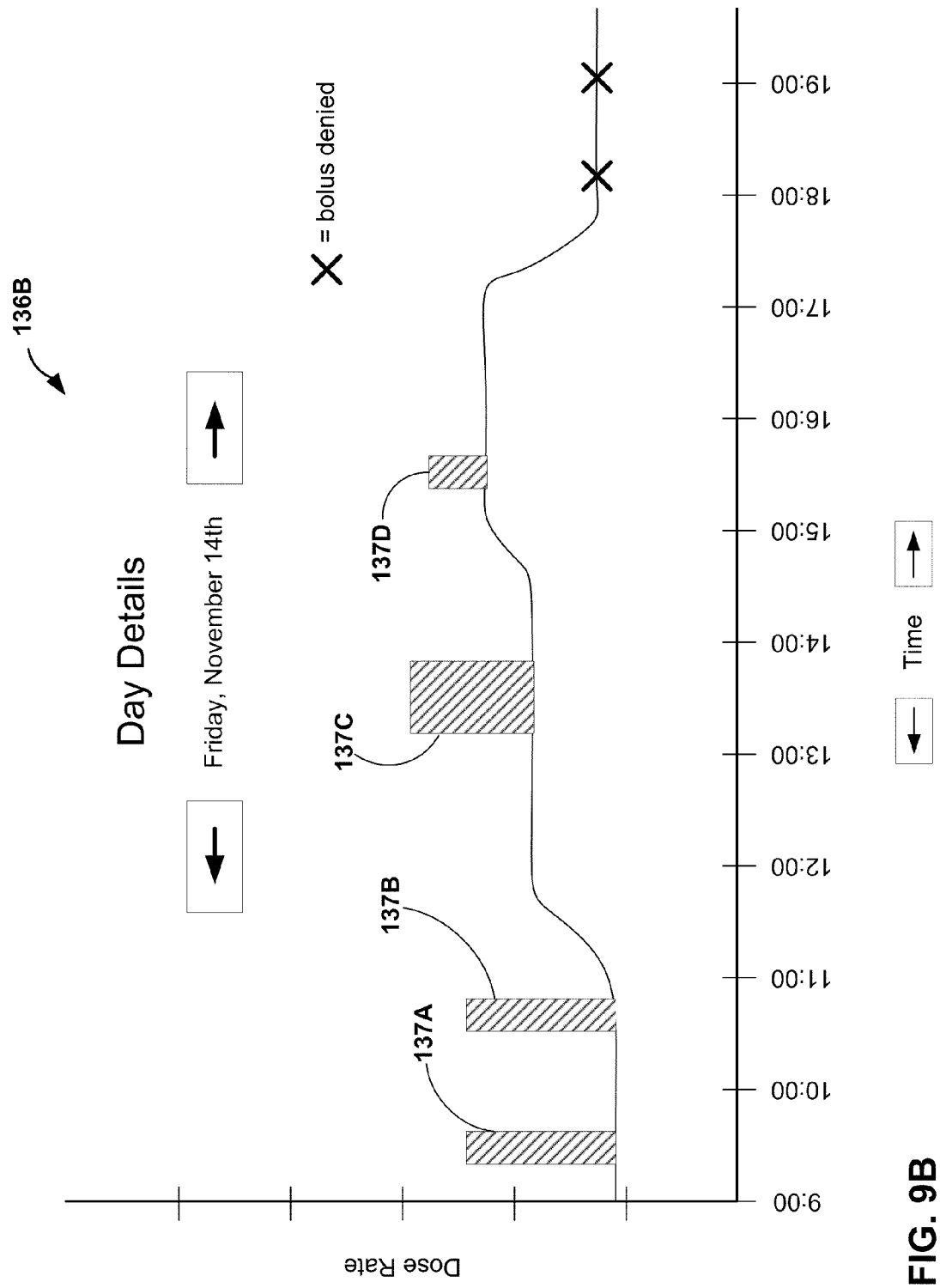

FIG. 9B illustrates an example of a day-view diagram 136B for a pump therapy, i.e., delivery of an agent. For the selected day, diagram 136B illustrates a basal rate 137 over time, and thereby illustrates at what times basal rate 137 is adjusted during the day. Diagram 136B also illustrates at what time boluses 138A-138D are delivered, and the amount of the boluses. Additional information about each of boluses 138A-138D may also be displayed, including bolus type and whether the bolus was programmed or patient-activated. In some embodiments, the basal rate may be zero and therapy may be delivered solely through boluses.

Furthermore, a diagram similar to 136B may be presented for each of a plurality of drugs or other agents, or a single diagram may depict one or both of a basal rate or boluses for one or more agents. In diagram 136B, for example, the basal rate 137 and boluses 138 may be for different agents. Diagram 136B may also illustrate if a bolus was requested but not delivered, e.g., if patient 12 requested additional boluses after a maximum daily dosage had already been reached. Like diagram 136A, diagram 136B may be used by the clinician to evaluate cyclical changes in the activity or symptoms of patient 12 throughout a day. Trends in the data illustrated by diagram 136B may suggest a particular activity or time of day for which new programs or groups would be beneficial.

Figure 10:
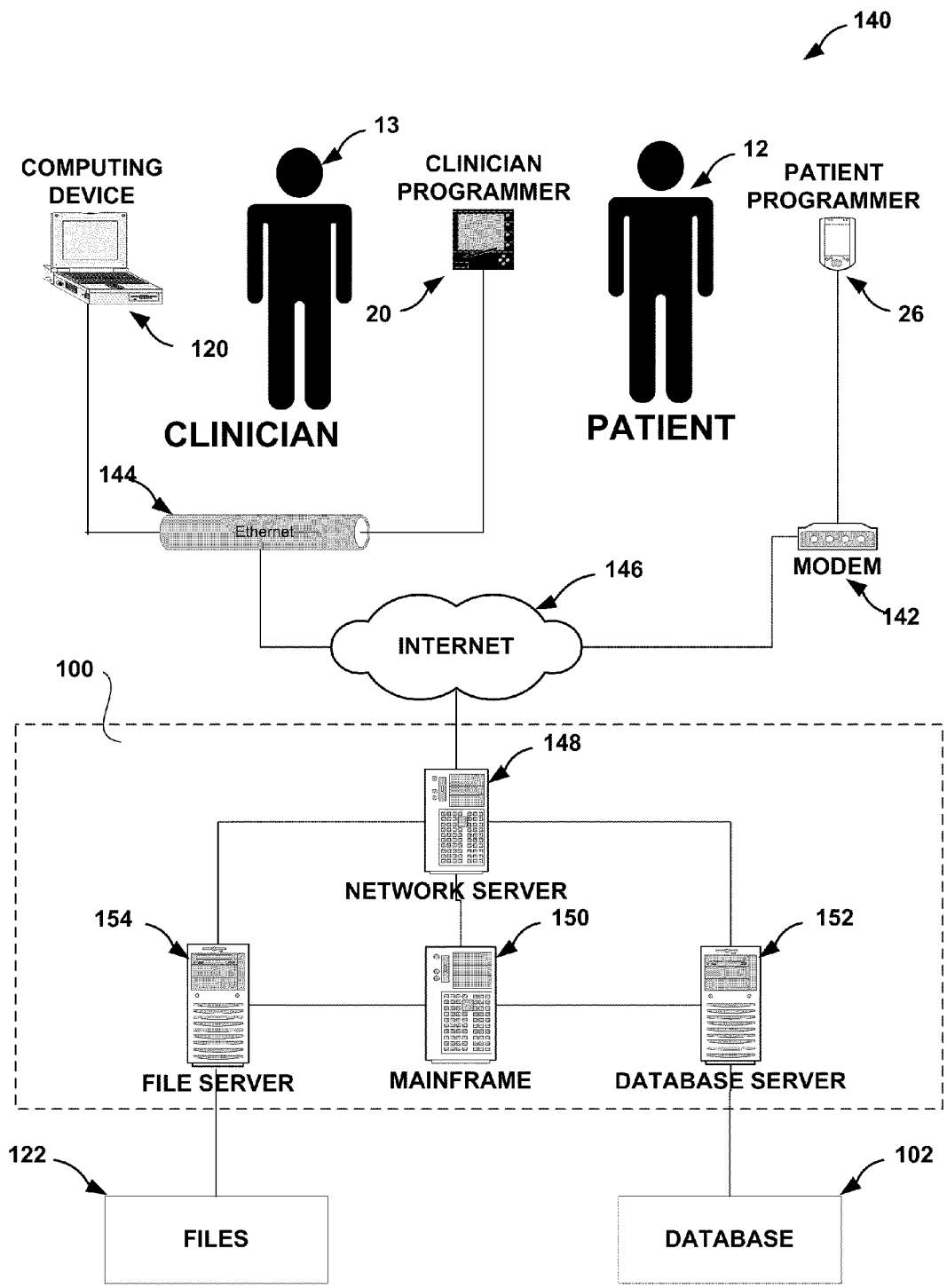
FIG. 10 is a conceptual diagram illustrating another example system that includes a remote networking device for managing usage information relating to therapy delivered to a patient.

FIG. 10 is a conceptual diagram illustrating another example system 140 for managing delivery of therapy to patient 12 and usage information for patient 12. Patient 12 interacts with patient programmer 26 that communicates with network server 148 through Internet 146 via a modem connection 142. A clinician 13 interacts with clinician programmer 20 or computing device 120 that communicates with network server 148 through the Internet 146 via an Ethernet connection 144. Network server 148 interacts with programming devices 20 and 26 and computing device 120, and also interacts with a mainframe 150, database server 152, and file server 154 to provide the functionality ascribed to server 100 above. Mainframe 150 may be a computer capable of substantial computation that analyzes information within database 102 to generate statistics 124 and other files 122. Database server 152 provides network server 148 and mainframe 150 with access to database 102, and creates and manages records within database 102. File server 154 manages files 122 and serves files to network server 148 upon request. Either or both of file server 154 and network server 148 may be web servers capable of serving web pages to client computing devices, such as programmers 20 and 26 and computing device 120.

Figure 11:
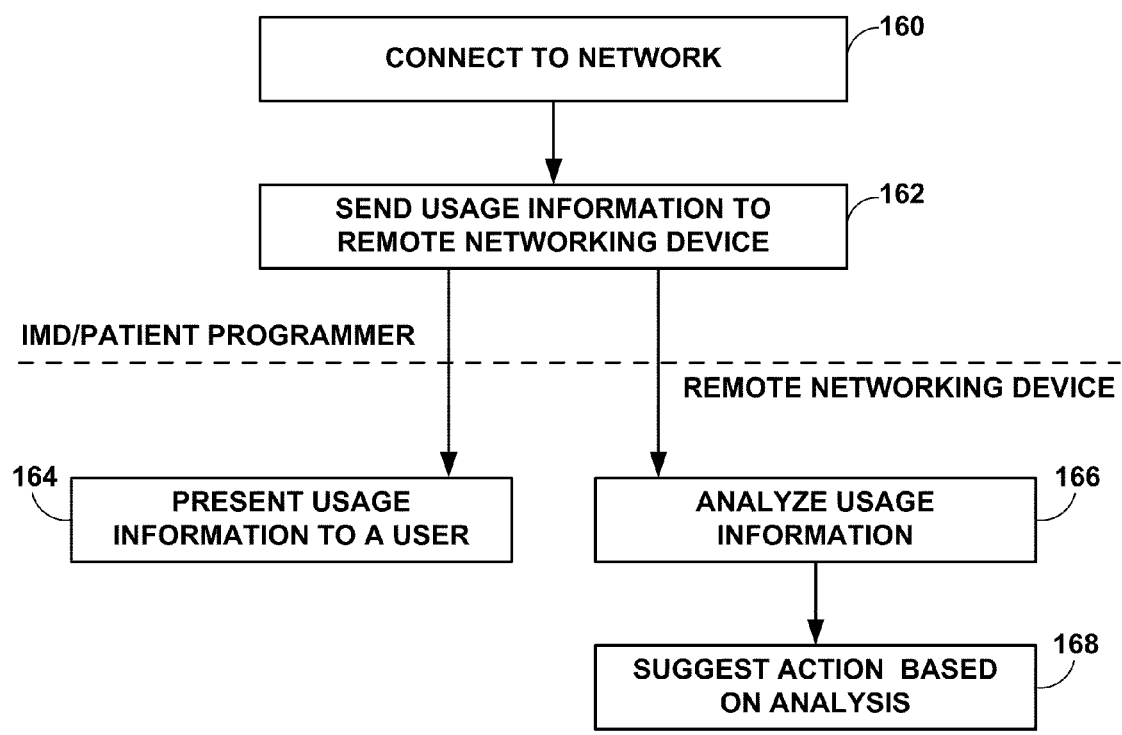
FIG. 11 is a flowchart illustrating an example method that may be employed by a system for managing usage information.

FIG. 11 is a flow chart illustrating an example method that may be employed by system 10 for managing usage information recorded by IMD 14 or patient programmer 26. The flow chart illustrated in FIG. 11 begins with IMD 14 or patient programmer 26 connecting to network 2 (160) and sending usage information 8 to remote networking device 4 via network 2 (162). Where patient programmer 26 stores usage information 8, patient programmer 26 may directly connect to network 2 or connect to network 2 via a linkage device, such as a base station that provides recharging features and a connection to network 2 as well as possibly other features, or a computing device, such as a laptop or desktop computer, a PDA, or a mobile communication device that execute therapy software and provide a connection to network 2.

Where IMD 14 stores usage information 8, IMD 8 may directly connect to network 2 to send usage information 8 to remote networking device 4. Alternatively, IMD 14 may connect to network 2 via a linkage device to send usage information to remote networking device 4. The linkage device may be patient programmer 26, a base station, or other previously described computing device in a home environment.

IMD 14 or patient programmer 26 may automatically send usage information 8 on a periodic basis, e.g., in accordance with a schedule, or when local memory is full. As another example, IMD 14 or patient programmer 26 may automatically send usage information 8 on an opportunistic basis, such as whenever IMD 14 or patient programmer 26 is within range of a computing device that provides a connection to network 2, such as a base station, desktop or laptop computer, or home monitor.

Upon receiving usage information 8, remote networking device 4 presents usage information 8 to a user (164), such as a clinician, technician, or manufacturer. Remote networking device 4 may include a screen or monitor for displaying usage information 8 or, alternatively, may send usage information 8 to an associated computing device for display, such as for display on a desktop computer monitor, a laptop screen, or a screen of clinician programmer 20. As previously described, usage information 8 may be presented as a diagram, graph, chart, histogram, or other graphical representation. Presenting usage information 8 to a user enables the user to take action based on the information. For example, a clinician may use usage information 8 that relates to use of therapy by patient 12 to select programs for use in long term programming of IMD 14 or modify program groups, programs, or therapy parameters. A clinician may also use this information to identify unexpected or undesirable therapy patterns, such as patient initiated therapy patterns that indicate drug seeking behavior or therapy patterns that indicate lack of use. In an additional example, a manufacturer may develop future products based on usage information 8 that relates to navigation patterns of a user interface of patient programmer 26 and information that relates to features of patient programmer 26.

In addition to presenting usage information 8 to a user, remote networking device 4 may also analyze usage information 8 (166) and suggest one or more actions based on the analysis (168). Remote networking device 8 may analyze usage information 8 based on a set of rules, by comparison to stored data, or both. Example actions that may be suggested by remote networking device 4 include programming guidance, or patient use guidance. Remote networking device 4 may also suggest that patient 12 visit a clinician if the identified problem cannot be resolved, or if a visit with a clinician is warranted. Suggesting an action may involve sending information to patient programmer 26 via network 2 and patient programmer 26 displaying the information to patient 12 by, for example, providing a text prompt on a screen.

Figure 12:
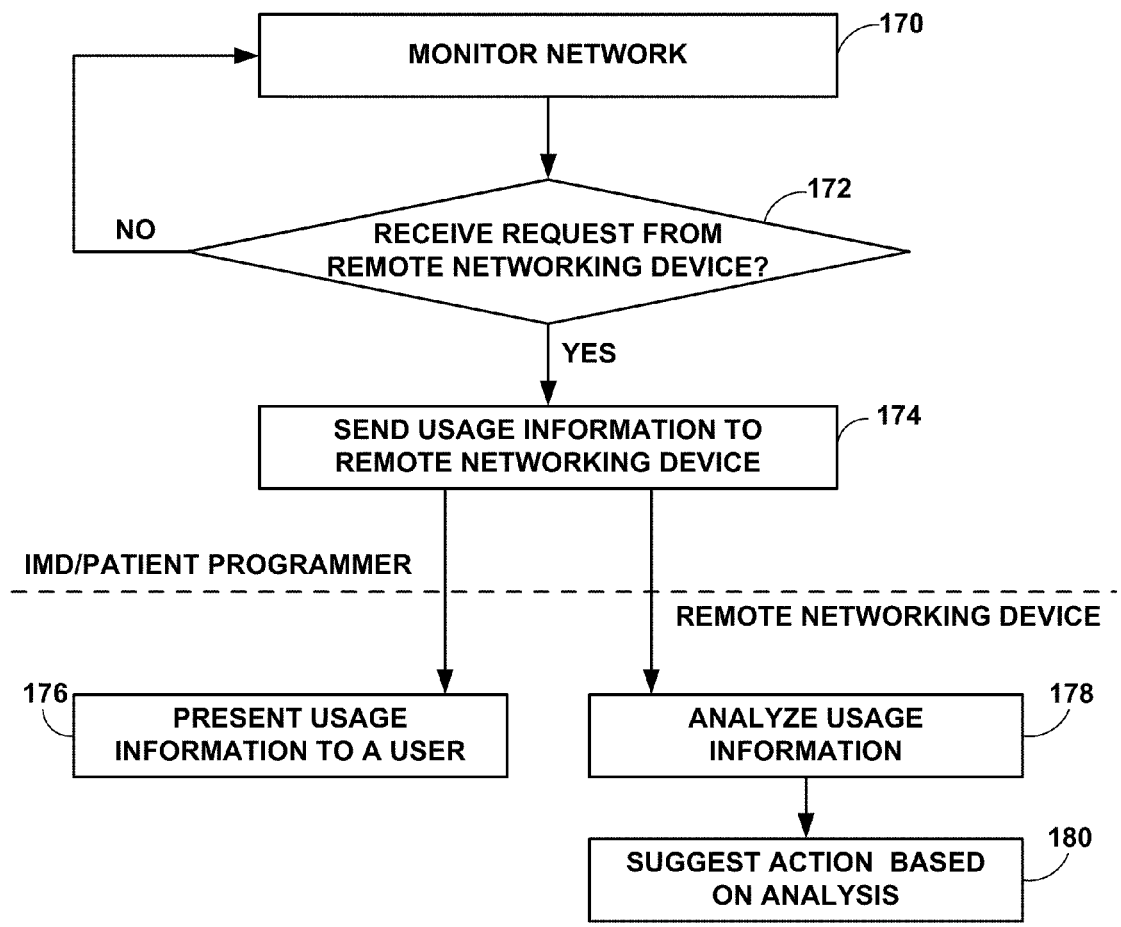
FIG. 12 is a flowchart illustrating another example method that may be employed by a system for managing usage information.

FIG. 12 is a flow chart illustrating another example method that may be employed by system 10 for managing usage information. The flow chart illustrated in FIG. 12 begins with IMD 14 or patient programmer 26 monitoring network 2 (170) for requests generated by remote networking device 4 (172). Remote networking device 4 may automatically generate requests, e.g., on a periodic basis, or may generate a request in response to receiving a command from a human administrator, such as a clinician, technician, or manufacturer. A human administrator may send a command to remote networking device 4 via a clinician programmer 20 or other associated programming device.

Patient programmer 26 or IMD 14 may monitor network 2 substantially continuously, i.e., may have a permanent connection to network 2, or may connect to network 2 and check for a request on a periodic basis. When a request is not received ("NO" branch of step 172), patient programmer 26 or IMD 14 continues to monitor network 2 (172). However, upon receiving a request from remote networking device 4 ("YES" branch of step 172), patient programmer 26 or IMD 14 sends usage information 8 to remote networking device 4 (174) via network 2.

As previously described with respect to FIG. 11, remote networking device 4 may present or analyze usage information 8 (176, 178, respectively) received via network 2 in step 174. Where remote networking device 4 analyzes usage information 8, remote networking device 4 suggests action based on the analysis (180).

Various embodiments of the invention have been described. These and other embodiments are within the scope of the following claims.

The invention claimed is:

1. A system comprising:
   a patient device that records usage information relating to the use, by a patient, of a therapy delivered by an implantable medical device to the patient; and
   a remote networking device that receives the usage information from the patient device via a network, wherein the remote networking device analyzes the received usage information, identifies a therapy usage pattern by the patient based on the analysis, and sends a control signal to the patient device when the therapy usage pattern indicates a use of the patient device that differs from an expected use, wherein the control signal is configured to limit programming of the implantable medical device by the patient device.

2. The system of claim 1, wherein the patient device comprises one of the implantable medical device or an external programming device that communicates with the implantable medical device via local, wireless communication.

3. The system of claim 1, and wherein the usage information relates to at least one of use of program groups by the patient, use of programs by the patient, adjustments to program groups by the patient, adjustments to programs by the patient, or overall use of therapy by the patient.

4. The system of claim 1, wherein the remote networking device presents the usage information to at least one of a clinician, a technician, or a manufacturer of the system.

5. The system of claim 1, wherein the remote networking device suggests therapy options based on the analysis of the received usage information.

6. The system of claim 5, wherein the remote networking device analyzes the received usage information to identify a frequently used program or program group and suggests therapy options that are similar to the frequently used program or program group.

7. The system of claim 5, wherein the remote networking devices analyzes received usage information to identify an infrequently used program or program group, and suggests therapy options by marking the infrequently used program or program group for removal from a list of programs or program groups used to provide therapy to the patient.

8. The system of claim 1, wherein the therapy usage pattern that indicates a use of the patient device that differs from an expected use comprises a therapy usage pattern that indicates undesirable drug seeking behavior.

9. The system of claim 1, wherein the control signal is configured to cause the patient device to operate in a locked state.

10. The system of claim 1, wherein the remote networking device identifies failure to use a trial program or program group based on the analysis.

11. The system of claim 1, wherein the remote networking device notifies, via the network, at least one of the patient or a clinician of the therapy usage pattern that indicates a use of the patient device that differs from an expected use.

12. The system of claim 1, wherein the remote networking device analyzes the received usage information by at least analyzing usage information received from the patient device over time, identifies a therapy usage pattern by the patient based on the analysis by at least identifying an established therapy usage pattern by the patient based on the analysis, receives subsequent usage information from the patient device, identifies changes from the established therapy usage pattern based on the subsequent usage information, and notifies at least one of the patient or a clinician of the changes via the network.

13. A method comprising:
receiving, at a remote networking device, usage information from a patient device via a network, wherein the usage information relates to the use, by a patient, of a therapy delivered by an implantable medical device to the patient;
analyzing the received usage information;
identifying a therapy usage pattern by the patient based on the analysis; and
sending a control signal to the patient device when the therapy usage pattern indicates a use of the patient device that differs from an expected use, wherein the control signal is configured to limit programming of the implantable medical device by the patient device.

14. The method of claim 13, wherein the usage information relates to at least one of use of program groups by the patient, use of programs by the patient, adjustments to program groups by the patient, adjustments to programs by the patient, or overall use of therapy by the patient.

15. The method of claim 13, further comprising presenting the usage information to at least one of a clinician, a technician, or a manufacturer of the system via the remote networking device.

16. The method of claim 13, further comprising suggesting therapy options by the remote networking device based on the analysis of the received usage information.

17. The method of claim 16, wherein analyzing the received usage information comprises identifying a frequently used program or program group, and suggesting therapy options comprises suggesting therapy options that are similar to the frequently used program or program group.

18. The method of claim 16, wherein analyzing the received usage information comprises identifying an infrequently used program or program group, and suggesting therapy options comprises marking the infrequently used program or program group for removal from a list of programs or program groups used to provide therapy to the patient.

19. The method of claim 13, wherein the therapy usage pattern that indicates a use of the patient device that differs from an expected use comprises a therapy usage pattern that indicates undesirable drug seeking behavior.

20. The method of claim 13, wherein the control signal is configured to cause the patient device to operate in a locked state.

21. The method of claim 13, wherein identifying a therapy usage pattern comprises identifying a failure to use a trial program or program group based on the analysis.

22. The method of claim 13, further comprising notifying, via the network, at least one of the patient or a clinician of the therapy usage pattern that indicates a use of the patient device that differs from an expected use.

23. The method of claim 13, wherein analyzing the received usage information comprises analyzing usage information received from the patient device over time, wherein identifying a therapy usage pattern by the patient based on the analysis comprises identifying an established therapy usage pattern by the patient based on the analysis, the method further comprising:
receiving subsequent usage information from the patient device;
identifying changes from the established therapy usage pattern based on the subsequent usage information; and
notifying at least one of the patient or a clinician of the changes via the network.

* * * * *